(12) United States Patent
Nohara et al.

(10) Patent No.: US 11,717,671 B2
(45) Date of Patent: Aug. 8, 2023

(54) BIOLOGICAL TISSUE TRANSDERMAL PATCH

(71) Applicant: Nippon Telegraph and Telephone Corporation, Tokyo (JP)

(72) Inventors: Masaya Nohara, Atsugi (JP); Mikayo Iwata, Atsugi (JP); Masahiko Hayashi, Atsugi (JP); Takeshi Komatsu, Atsugi (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 577 days.

(21) Appl. No.: 16/606,403

(22) PCT Filed: Apr. 18, 2018

(86) PCT No.: PCT/JP2018/015962
§ 371 (c)(1),
(2) Date: Oct. 18, 2019

(87) PCT Pub. No.: WO2018/194079
PCT Pub. Date: Oct. 25, 2018

(65) Prior Publication Data
US 2020/0121915 A1 Apr. 23, 2020

(30) Foreign Application Priority Data

Apr. 21, 2017 (JP) .................. 2017-084340
Apr. 21, 2017 (JP) .................. 2017-084345

(51) Int. Cl.
*A61N 1/04* (2006.01)
*A61K 9/00* (2006.01)
*A61K 9/70* (2006.01)

(52) U.S. Cl.
CPC .......... *A61N 1/0448* (2013.01); *A61K 9/0009* (2013.01); *A61K 9/7084* (2013.01); *A61N 1/0432* (2013.01)

(58) Field of Classification Search
CPC .. A61N 1/0448; A61N 1/0432; A61K 9/0009; A61K 9/7084
See application file for complete search history.

(56) References Cited

U.S. PATENT DOCUMENTS

| 5,037,381 A | 8/1991 | Bock et al. |
| 5,645,527 A | 7/1997 | Beck |
| 6,171,294 B1 * | 1/2001 | Southam .................. A61N 1/30 604/20 |
| 7,340,310 B2 * | 3/2008 | Nitzan .................... H01M 4/38 607/152 |
| 2013/0202954 A1 * | 8/2013 | Suzuki .................... H01M 4/38 429/188 |
| 2013/0280334 A1 * | 10/2013 | Karp .................... A61K 31/405 424/490 |
| 2015/0246215 A1 | 9/2015 | Yaegashi et al. |

FOREIGN PATENT DOCUMENTS

| EP | 0468430 | * | 7/1991 |
| EP | 0468430 A2 | | 1/1992 |
| EP | 1902749 | * | 9/2007 |
| EP | 2939705 A1 | | 11/2015 |
| JP | H04-236969 A | | 8/1992 |
| JP | 11-503956 A | | 4/1999 |
| JP | 2006-247242 A | | 9/2006 |
| JP | 2007-68969 A | | 3/2007 |
| JP | 2014-207987 A1 | | 11/2014 |
| JP | 2014207987 A | | 11/2014 |
| WO | 2014/102896 A1 | | 7/2014 |

OTHER PUBLICATIONS

Josh et al. Design and Functionality (pain Management ; 6(2); 2016).*
Ogawa et al., "Organic Transdermal Iontophoresis Patch with Built-in Biofuel Cell", Advanced Healthcare Materials, WILEY-VCH Verlag GmbH & Co. KGaA, Weinheim, 2015, vol. 4, Issue 4, pp. 506-510.
International Search Report, PCT Patent Application No. PCT/JP2018/015962, dated Jul. 24, 2018.
Written Opinion, PCT Patent Application No. PCT/JP2018/015962, dated Jul. 24, 2018.
International Preliminary Report on Patentability, PCT Patent Application No. PCT/JP2018/015962, dated Oct. 31, 2019.

* cited by examiner

*Primary Examiner* — Shirley V Gembeh
(74) *Attorney, Agent, or Firm* — Kilpatrick Townsend & Stockton, LLP

(57) ABSTRACT

A biological tissue transdermal patch houses a battery part and an active ingredient such that they do not come into contact with each other. For the use of the biological tissue transdermal patch, the battery part and the active ingredient are brought into contact to start battery reaction of the battery part and the battery part is attached to a biological tissue. Carbonized bacterial cellulose or cellulose nanofiber carbon is used for a positive electrode of the battery part.

9 Claims, 13 Drawing Sheets

BIOLOGICAL TISSUE TRANSDERMAL PATCH

TECHNICAL FIELD

The present invention relates to a biological tissue transdermal patch which is attached to a biological tissue and causes an active ingredient to penetrate into the biological tissue by using microcurrent and a battery which is included in the biological tissue transdermal patch.

BACKGROUND ART

Cosmetics and medications in forms of liquid and cream are widely popular. A method of causing an active ingredient in a cosmetic or a medication to penetrate into a living body by using microcurrent has been drawing attention. The method using microcurrent is known to be promising to produce effects of activating the cells and improving penetration of a drug. However, this method requires an expensive large power supply device.

In order to solve these problems, there is known a biological tissue transdermal patch including a power supply device using a general dry-cell battery. However, since the power supply device using a general dry-cell battery uses harmful material, rare metals, and the like in the dry-cell battery and the power supply device, this technique has problems to solve such as reduction of environmental load and simplification of disposal.

A biological tissue transdermal patch which requires no power supply device and has low environmental load is also known (non-patent document 1).

PRIOR ART DOCUMENT

Non-Patent Document

Non-patent document 1: Yudai Ogawa, Koichiro Kato, Takeo Miyake, Kuniaki Nagamine, Takuya Ofuji, Syuhei Yoshino, and Matsuhiko Nishizawa, "Organic Transdermal Iontophoresis Patch with Built-in Biofuel Cell", Advanced Healthcare Materials, WILEY-VCH Verlag GmbH & Co. KGaA, Weinheim, 2015, Volume 4, Issue 4, pp. 506-510

SUMMARY OF THE INVENTION

Problem to be Solved by the Invention

The biological tissue transdermal patch of non-patent document 1 includes a biofuel cell. In the biological tissue transdermal patch of non-patent document 1, an active ingredient to penetrate into the tissue needs to be used in a gel form or be manually applied so as not to form liquid junction between a positive electrode and a negative electrode.

When the active ingredient is used in a gel form, the biological tissue transdermal patch needs to be stored in a state where the active ingredient is arranged in contact with the positive electrode and the negative electrode. Moreover, many of liquid and cream chemical products which are commercially available and widely used require a step of gelling.

Moreover, the biological tissue transdermal patch during the storage has problems of self-discharging of the battery part and corrosion caused by continuous contact of the active ingredient with the positive electrode and the negative electrode.

Meanwhile, when the active ingredient is to be applied, the user needs to carefully apply the active ingredient so as not to form a liquid junction between the positive electrode and negative electrode and this troublesome step is a burden on the user.

The present invention has been made in view of the aforementioned circumstances and an objective thereof is to provide a biological tissue transdermal patch which requires no change in the form of many of commercially-available, widely-used liquid and cream chemical products and which can suppress self-discharging of a battery part while maintaining an active ingredient to be introduced into a biological tissue in a fresh state during storage.

Means for Solving the Problem

In order to solve the aforementioned problems, a biological tissue transdermal patch according to the present invention is a biological tissue transdermal patch which is to be used by being attached to a biological tissue, comprising: a battery part; and an active ingredient which is housed out of contact with the battery part, and for use of the biological tissue transdermal patch, the active ingredient is brought into contact with the battery part to start battery reaction.

Effect of the Invention

The present invention can provide a biological tissue transdermal patch which requires no change in the form of many of commercially-available, widely-used liquid and cream chemical products and which can suppress self-discharging of a battery part while maintaining an active ingredient to be introduced into a biological tissue in a fresh state during storage.

MODE FOR CARRYING OUT THE INVENTION

An embodiment of the present invention is described below with reference to the drawings.
(Configuration of Biological Tissue Transdermal Patch)

A biological tissue transdermal patch of the embodiment is a patch which causes an active ingredient to penetrate into a biological tissue by using electricity generated by a reaction similar to that in a general magnesium-air battery.

Figure 1:
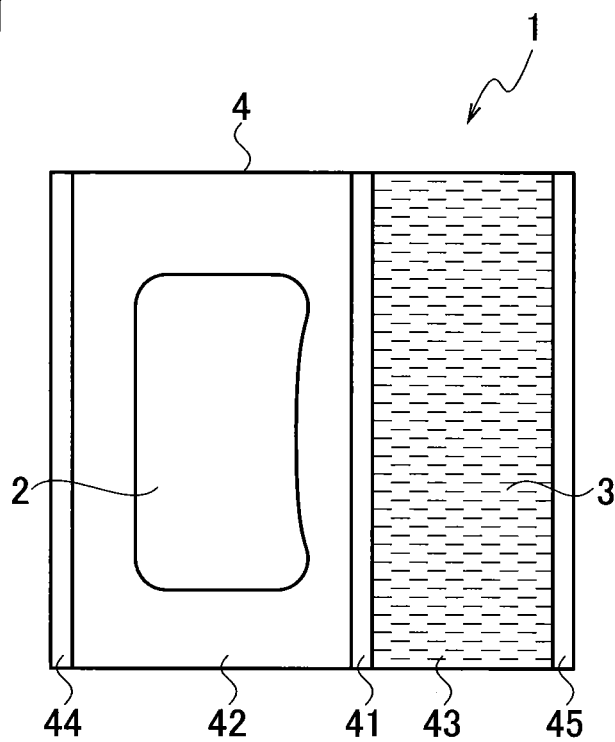
FIG. 1 is a plan view illustrating a configuration of a biological tissue transdermal patch in the embodiment.

FIG. 1 is a plan view illustrating a configuration of the biological tissue transdermal patch in the embodiment. The biological tissue transdermal patch 1 illustrated in FIG. 1 includes a battery part 2 and an active ingredient 3. The battery part 2 and the active ingredient 3 are housed in a plastic pack 4 while being isolated from each other. The battery part 2 does not include electrolyte necessary in a general battery and is stored in a state where no battery reaction occurs. The active ingredient 3 may take any of forms of liquid, cream, and gel as long as the active ingredient 3 works as the electrolyte of the battery part 2 when the biological tissue transdermal patch 1 is used. For example, when the separator of the battery part 2 is impregnated with the active ingredient 3, the active ingredient 3 works as the electrolyte and the battery reaction starts.

The plastic pack 4 includes a battery part storage 42 housing the battery part 2 and an active ingredient storage 43 housing the active ingredient 3. The battery part storage 42 and the active ingredient storage 43 are isolated from each other by a partition wall 41. Both ends 44, 45 of the plastic pack 4 are sealed by thermal sealing. Various materials such as, for example, vinyl-based, polystyrene-based, and acryl-based materials can be used as the material of the plastic pack 4. More specifically, the examples of the material include polyvinyl chloride, polyvinylidene chloride, polyvinyl alcohol, polystyrene, styrene acrylonitrile copolymer, styrene butadiene acrylonitrile copolymer, high-density polyethylene, medium-density polyethylene, low-density polyethylene, ethylene-vinyl acetate copolymer, polypropylene, homopolymer polyacetal, copolymer polyacetal, polymethylmethacrylate, polyester, PPS, polypropylene, cellophane, acetate, polycarbonate, nylon, and polyimide.

The partition wall 41 is not limited to a particular wall as long as the battery part 2 and the active ingredient 3 can be housed while being isolated from each other. For example, the battery part storage 42 and the active ingredient storage 43 are preferably isolated from each other by thermal sealing, adhesive, or chucking. The thermal sealing is particularly preferable from the viewpoint of cost and a degree of complication in manufacturing.

The biological tissue transdermal patch 1 may include structural members such as an outer film, a case, adhesive, and metal foil and elements necessary for a general magnesium-air battery, in addition to the configuration described above. Publicly-known members and elements may be used as these members and elements.

Figure 2:
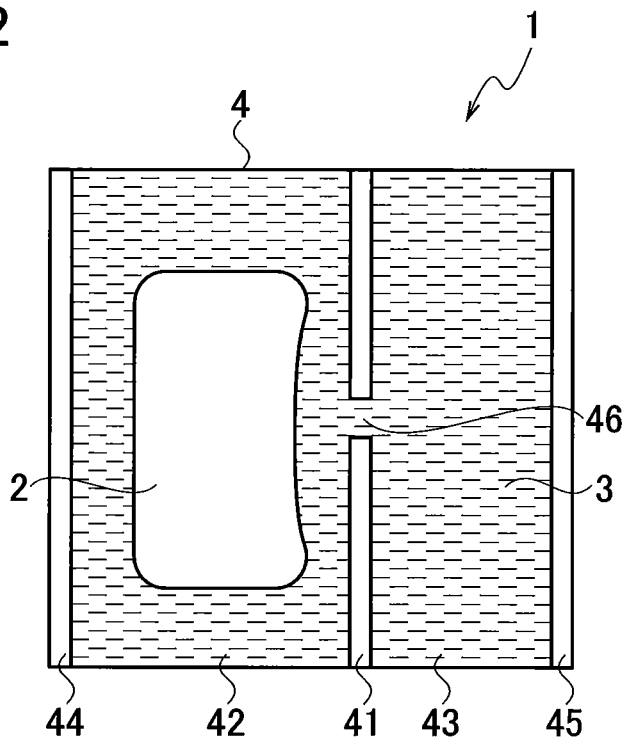
FIG. 2 is a view illustrating how a partition wall of the biological tissue transdermal patch in FIG. 1 is broken and an active ingredient is brought into contact with a battery part.

For use of the biological tissue transdermal patch 1, the active ingredient 3 is brought into contact with the battery part 2. The active ingredient 3 serves the same role as the electrolyte and the battery reaction starts in the battery part 2. For example, as illustrated in FIG. 2, the partition wall 41 is broken to form an opening hole 46 and the active ingredient 3 is brought into contact with the battery part 2. A method of pressing the active ingredient storage 43 storing the active ingredient 3 with the finger and applying pressure thereto is preferable as the method of breaking the partition wall 41 due to easiness and low cost. When the pressure is insufficient and the partition wall 41 is not broken, the active ingredient storage 43 is folded in half and pressed. This increases the pressure and the partition wall 41 can be broken. The method of breaking the partition wall 41 is not limited to a particular method. Examples of the method of breaking the partition wall 41 include a method of opening a hole with a needle, a toothpick, or the like with a sharp tip, a method of cutting the partition wall 41 with a pair of scissors or the like, and a method of tearing the partition wall 41 with the hands.

Figure 3:
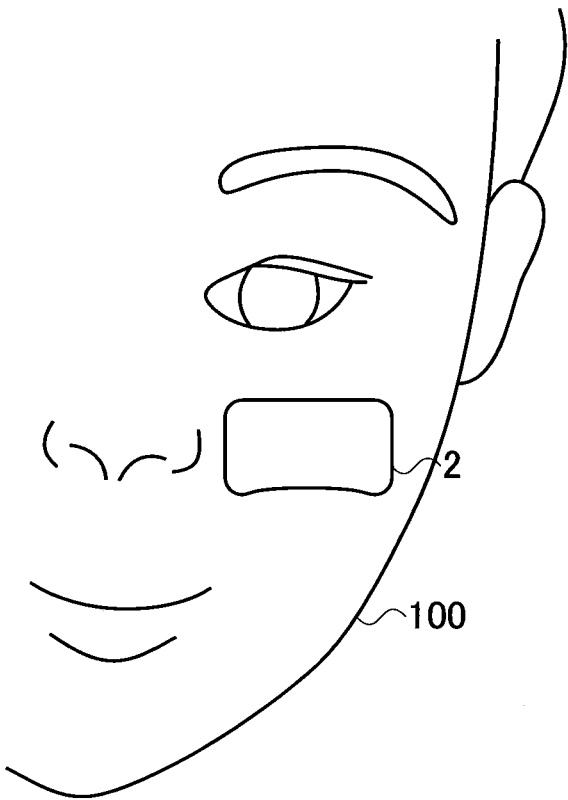
FIG. 3 is a view illustrating how the battery part in FIG. 2 is attached to a biological tissue and used.

After the battery reaction is started, as illustrated in FIG. 3, the battery part 2 is taken out from the battery part storage 42 and is used by being attached to a biological tissue 100. The shapes of the biological tissue transdermal patch 1 and the battery part 2 are not limited to particular shapes. For example, the biological tissue transdermal patch 1 and the battery part 2 may have a shape of a patch, a facemask, an eye mask, a glove, a bandage, an adhesive bandage, or a poultice.
(Configuration of Battery Part)

Next, a configuration of the battery part 2 is described.

Figure 4:
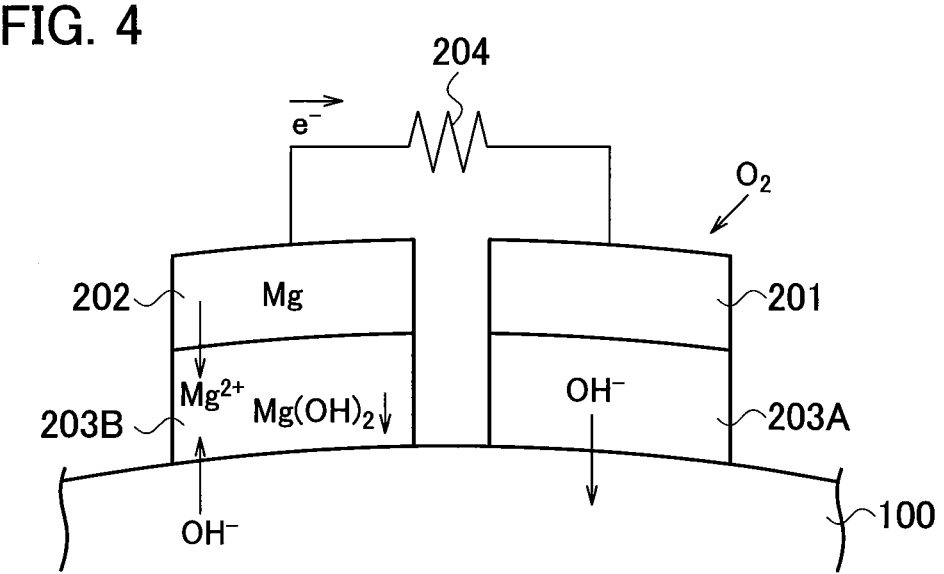
FIG. 4 is a view schematically illustrating a configuration of a battery part in which a separator is divided into a positive electrode separator and a negative electrode separator.

FIG. 4 is a view schematically illustrating an example of a configuration of the battery part 2 in which a separator is divided into a positive electrode separator and a negative electrode separator.

The battery part 2 of FIG. 4 includes a positive electrode 201, a negative electrode 202 containing magnesium, a positive electrode separator 203A arranged in contact with the positive electrode 201 and out of contact with the negative electrode 202, a negative electrode separator 203B arranged in contact with the negative electrode 202 and out of contact with the positive electrode 201, and an electrically-conductive layer 204 electrically connecting the positive electrode 201 and the negative electrode 202 to each other. Unlike the general magnesium-air battery, in the battery part 2 of FIG. 4, the positive electrode separator 203A and the negative electrode separator 203B are out of contact with each other and include no electrolyte. The battery part 2 of FIG. 4 is used with the positive electrode separator 203A and the negative electrode separator 203B attached to the biological tissue 100.

Figure 5:
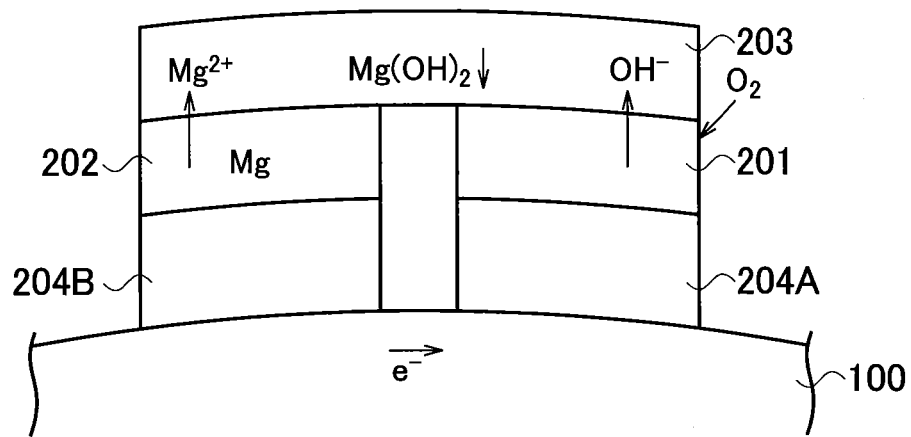
FIG. 5 is a view schematically illustrating a configuration of a battery part in which an electrically-conductive layer is divided into a positive electrode electrically-conductive layer and a negative electrode electrically-conductive layer.

FIG. 5 is a view schematically illustrating an example of a configuration of the battery part 2 in which an electrically-conductive layer is divided into a positive electrode electrically-conductive layer and a negative electrode electrically-conductive layer.

The battery part 2 of FIG. 5 includes the positive electrode 201, the negative electrode 202 containing magnesium, a separator 203 arranged to be in contact with the positive electrode 201 and the negative electrode 202, a positive electrode electrically-conductive layer 204A arranged in contact with the positive electrode 201 and out of contact with the negative electrode 202, and a negative electrode electrically-conductive layer 204B arranged in contact with the negative electrode 202 and out of contact with the positive electrode 201. Unlike the general magnesium-air battery, in the battery part 2 of FIG. 5, the separator 203 includes no electrolyte. The battery part 2 of FIG. 5 is used with the positive electrode electrically-conductive layer 204A and the negative electrode electrically-conductive layer 204B attached to the biological tissue 100.

Note that, as another example of a configuration of the battery part 2, the separator 203 or the electrically-conductive layer 204 may not be divided into portions for the positive electrode and the negative electrode.

Electrode reactions in the positive electrode 201 and the negative electrode 202 are described.

Water contained in the active ingredient 3 and oxygen in air come into contact on a surface of the positive electrode 201 and the reaction illustrated in the following formula (1) progresses.

$$O_2 + 2H_2O + 4e^- \rightarrow 4OH^- \quad (1)$$

Meanwhile, in the negative electrode 202 in contact with the active ingredient 3, the reaction illustrated in the following formula (2) progresses. Specifically, magnesium forming the negative electrode 202 discharges electrons and dissolves into the active ingredient 3 as magnesium ions.

$$Mg \rightarrow Mg^{2+} + 2e^- \quad (2)$$

These reactions occur via the biological tissue 100. In the battery part 2 of FIG. 4, the active ingredient 3 impregnated into the positive electrode separator 203A is introduced into the biological tissue 100 together with hydroxide ions (OH⁻). In the battery part 2 of FIG. 5, when the reactions of formulae (1) and (2) progress, electrons (electric current) flow into the biological tissue 100. With the flow of electrons into the biological tissue 100, anionic species and cationic species of the active ingredient 3 penetrate into the biological tissue 100.

The entire reaction of the battery reactions is as illustrated in the following formula (3) and is a reaction of generating magnesium hydroxide.

$$2Mg + O_2 + 2H_2O \rightarrow 2Mg(OH)_2 \quad (3)$$

Theoretical electromotive force is about 2.7 V. FIGS. 4 and 5 illustrate compounds relating to the reactions together with the elements forming the battery part 2.

The elements forming the battery part 2 are as follows.

(I) Positive Electrode

A positive electrode used in a general magnesium-air battery may be used as the positive electrode 201. For example, carbon, metal, oxide, nitride, carbide, sulfide, or phosphide may be used. Two or more of these materials may be mixed. The positive electrode 201 is fabricated in publicly-known processing of shaping carbon powder with a binder. A resin containing fluorine is generally used as the binder. Accordingly, when the positive electrode 201 is combusted in disposal or the like, hydrofluoric acid is generated. Thus, there is room for improvement such as an improvement in safety and reduction of environmental load. In the embodiment, carbonized bacterial cellulose or cellulose nanofiber carbon is used for the positive electrode 201 and no resin containing fluorine is used. The carbonized bacterial cellulose used for the positive electrode 201 has a three-dimensional network structure of carbonized bacterial cellulose and has, for example, an average pore diameter of preferably 0.1 to 50 µm, more preferably, 0.1 to 2 µm. The average pore diameter is a value obtained by mercury intrusion porosimetry. The cellulose nanofiber carbon used for the positive electrode 201 has a three-dimensional network structure of carbonized cellulose nanofiber and has, for example, a fiber diameter of preferably 5 to 500 nm, more preferably, 20 to 200 nm.

The positive electrode 201 may support a catalyst. The catalyst is metal, oxide, nitride, carbide, sulfide, or phosphide. Two or more of these materials may be mixed. Iron, manganese, copper, nickel, silver, gold, platinum, cobalt, ruthenium, molybdenum, titanium, chrome, gallium, praseodymium, aluminum, silicon, or tin may be used as the metal. An alloy containing two or more of these metals may be used. An oxide of one of the aforementioned metals or a complex oxide of two or more of the aforementioned metals is preferable as the oxide. Particularly, iron oxide ($Fe_2O_3$) is preferable. Iron oxide is preferable in the point that the iron oxide has a particularly excellent catalyst performance and is not a rare metal. The metal oxide used as the catalyst is preferably an amorphous hydrate. For example, the metal oxide used as the catalyst may be a hydrate of the transition metal oxide described above. More specifically, the metal oxide used as the catalyst may be iron oxide (III)-n hydrate. Note that n is the number of moles of $H_2O$ with respect to one mole of $Fe_2O_3$.

Attaching (adding) nano-sized fine particles of iron oxide hydrate ($Fe_2O_3 \cdot nH_2O$) in high dispersion on a surface of the carbonized bacterial cellulose of the positive electrode 201 can cause the positive electrode 201 to exhibit excellent performance. The content of the catalyst contained in the positive electrode 201 is 0.1 to 70 wt %, preferably 1 to 30 wt % based on the total weight of the positive electrode 201. Adding the transition metal oxide to the positive electrode 201 as the catalyst greatly improves the performance of the battery part 2.

The reaction illustrated in the aforementioned formula (1) progresses on the surface of the positive electrode 201. Accordingly, it is important to generate many reaction sites inside the positive electrode 201 and the positive electrode 201 desirably has a high specific surface area. For example, the positive electrode 201 has a specific surface area of preferably 200 m²/g or more, more preferably 300 m²/g or more.

(II) Negative Electrode

The negative electrode 202 is made of a negative electrode active material. The negative electrode active material may be any material which can be used as a negative electrode material of a magnesium-air battery, that is a material containing metal magnesium or a magnesium-containing substance. The negative electrode 202 may be formed of, for example, metal magnesium, a sheet of metal magnesium, or magnesium powder. Materials other than magnesium which can be used for a metal-air battery such as iron, zinc, aluminum, calcium, lithium, and sodium may be also used as the negative electrode material. Use of magnesium is most preferable from the viewpoint of safety and battery output.

(III) Separator

The material of the separator 203, the positive electrode separator 203A, and the negative electrode separator 203B may be any material which can contain the active ingredient 3 and has no electrical conductivity. For example, Japanese paper, cotton, collagen, bacterial gel, or bacterial xerogel may be used. Since the bacterial xerogel is porous, the bacterial xerogel has a high performance of holding the active ingredient 3. Since the bacterial xerogel turns into gel when holding the active ingredient 3, the bacterial xerogel has excellent adhesion to a biological tissue.

In the battery part 2 in which the separator is to be attached to the biological tissue, it is preferable that the separator is divided into the positive electrode separator 203A and the negative electrode separator 203B and the separators 203A and 203B are out of contact with each other as in the battery part 2 of FIG. 4. This is because, when the positive electrode separator 203A and the negative electrode separator 203B are in contact with each other, the battery reaction progresses without involving the biological tissue and the ion introduction effect of the active ingredient 3 decreases.

(IV) Electrically-Conductive Layer

The material of the electrically-conductive layer 204, the positive electrode electrically-conductive layer 204A, and the negative electrode electrically-conductive layer 204B is not limited to a particular material and may be any material as long as it is electrically conductive. Examples of the material include a carbon cloth, a carbon sheet, a carbon mesh, a metal mesh, a metal wire, an electrically-conductive cloth, an electrically-conductive rubber, and an electrically-conductive polymer. Adjusting the electrical resistance value of the electrically-conductive layer 204 can adjust the rate of the battery reaction. Increasing the resistance value of the electrically-conductive layer 204 slows the rate of the ion introduction of the active ingredient 3. When the ion introduction is too quick and a user feels pain, it is only necessary to increase the resistance value of the electrically-conductive layer 204.

In the battery part 2 in which the separator is to be attached to the biological tissue, the electrically-conductive layer 204 having a liquid repelling performance can be further improve the performance of the biological tissue transdermal patch 1. When the electrically-conductive layer 204 has no liquid repelling performance, the electrically-conductive layer 204 absorbs the active ingredient 3 and the battery reaction progresses without involving the biological tissue. As a result, the ion introduction effect of the active ingredient 3 decreases. The electrically-conductive layer 204 may be coated with a plastic film, a silicon-based silane compound, a fluorine-based resin, or a metal film to have a liquid repelling performance. The plastic film is preferable due to low cost and excellent processability. Various materials such as vinyl-based, polystyrene-based, and acryl-based materials may be used for the plastic film. Specifically, examples of the material include polyvinyl chloride, polyvinylidene chloride, polyvinyl alcohol, polystyrene, styrene acrylonitrile copolymer, styrene butadiene acrylonitrile copolymer, high-density polyethylene, medium-density polyethylene, low-density polyethylene, ethylene-vinyl acetate copolymer, polypropylene, homopolymer polyacetal, copolymer polyacetal, polymethylmethacrylate, polyester, PPS, polypropylene, cellophane, acetate, polycarbonate, nylon, and polyimide.

In the battery part 2 in which the electrically-conductive layer is to be attached to the biological tissue, it is preferable that the electrically-conductive layer is divided into the positive electrode electrically-conductive layer 204A and the negative electrode electrically-conductive layer 204B and the electrically-conductive layers 204A and 204B are out of contact with each other as in the battery part 2 of FIG. 5. This is because, when the positive electrode electrically-conductive layer 204A and the negative electrode electrically-conductive layer 204B are in contact with each other, the battery reaction progresses without involving the biological tissue and the ion introduction effect of the active ingredient 3 decreases.

(Regarding Active Ingredient)

Next, the active ingredient is described.

The "active ingredient" of the embodiment refers to water, alcohol, a drug solution which has an effect on a specific disease, or a cosmetic liquid which is used to clean and beautify the body of a human, make a person more attractive, change the appearance, and maintain the skin or hair healthy.

The active ingredient 3 may be any material in which magnesium ions and hydroxide ions are movable between the positive electrode 201 and the negative electrode 202 via the biological tissue 100 or the separator 203.

Examples of the active ingredient include organic and inorganic acids, derivatives thereof, and solution containing salts of these acids. Examples of the active ingredient include anion species such as amino acid ions, chloride ions, citrate ions, lactate ions, succinate ions, phosphate ions, malate ions, pyrrolidone carboxylic acid ions, sulfocarbolic acid ions, sulfite ions, nitrate ions, carbonate ions, and perchloric acid ions. Examples of the amino acid include glycine, alanine, valine, leucine, isoleucine, phenylalanine, tyrosine, threonine, serine, proline, tryptophan, methionine, cysteine, aspartic acid, glutamic acid, asparagine, glutamine, lysine, arginine, histidine, hydroxyproline, cysteine, and thyroxine.

Examples of the cationic species include potassium ions, sodium ions, lithium ions, calcium ions, magnesium ions, and zinc ions.

Specific examples of the active ingredient include sodium salt of amino acid, sodium chloride, potassium chloride, magnesium chloride, sodium citrate, magnesium citrate, sodium lactate, magnesium lactate, calcium lactate, sodium succinate, magnesium succinate, sodium malate, magnesium malate, sodium pyrrolidone carboxylate, magnesium pyrrolidone carboxylate, zinc sulfocarbolate, aluminum potassium sulfate (alum), sea water, and hot spring water.

Moreover, an active ingredient in which the magnesium ions and the hydroxide ions do not move may contain sodium salt of amino acid, sodium chloride, potassium chloride, magnesium chloride, sodium citrate, magnesium citrate, sodium lactate, magnesium lactate, calcium lactate, sodium succinate, magnesium succinate, sodium malate, magnesium malate, sodium pyrrolidone carboxylate, magnesium pyrrolidone carboxylate, zinc sulfocarbolate, aluminum potassium sulfate (alum), sea water, and hot spring water described above to allow the magnesium ions and the hydroxide ions to move. The method of making the effective ingredient additionally contain sodium salt of amino acid, sodium chloride, potassium chloride, magnesium chloride, sodium citrate, magnesium citrate, sodium lactate, magnesium lactate, calcium lactate, sodium succinate, magnesium succinate, sodium malate, magnesium malate, sodium pyrrolidone carboxylate, magnesium pyrrolidone carboxylate, zinc sulfocarbolate, aluminum potassium sulfate (alum), sea water, or hot spring water as described above enables almost all of commercially-available medical drugs, quasi-drugs, cosmetics, and supplements to be used as the effective ingredient.

Examples of medical drugs, quasi-drugs, cosmetics, and supplements include the following substances.

Examples of substances with anti-aging effects include uric acid, glutathione, melatonin, polyphenol, melanoidin, astaxanthin, kinetin, epigallocatechin gallate, coenzyme Q10, vitamins, superoxide dismutase, mannitol, quercetin, catechin and its derivatives, rutin and its derivatives, moutan bark extract, Alnus firma fruit extract, Melissa extract, Siraitia grosvenorii extract, dibutylhydroxytoluene, and butylated hydroxyanisole.

Substances with whitening effects include whitening agent and anti-inflammatory agent. The whitening agent has an effect of preventing darkening of the skin due to sunburn and formation of spots and freckles caused by pigment deposition. Examples of the whitening agent include arbutin, ellagic acid, linoleic acid, vitamin C and its derivatives, kojic acid, tranexamic acid, placenta extract, German chamomile extract, Glycyrrhiza extract, Rosa multiflora extract, Scutellaria root extract, seaweed extract, Sophora root extract, Spatholobi caulis extract, Eleuterococcus extract, rice bran extract, wheat germ extract, Asiasarum root extract, Cragaegus fruit extract, Cassia mimosoides extract, white lily extract, Paeoniae radix extract, Inula flower extract, soybean extract, tea extract, molasses extract, Ampelopsis japonica extract, grape extract, common hop extract, Rosa rugose extract, Chaenomeles lagenaria extract, and Saxifraga stolonifera extract. The anti-inflammatory agent has an effect of suppressing burning of the skin after sunburn and inflammatory of erythema. Examples of the anti-inflammatory agent include sulfur and its derivatives, glycyrrhizic acid and its derivatives, glycyrrhetinic acid and its derivatives, althaea extract, Angelica keiskei extract, German chamomile extract, Lonicera japonica extract, Nasturtium officinale extract, comfrey extract, salvia extract, Lithospermum root extract, shiso extract, white birch extract, and gentian extract.

Examples of substances with pealing and brightening effects include α-hydroxy acid, salicylic acid, sulfur, and uric acid.

Examples of substances with a slimming effect include substances with an effect of improving blood circulation and the like, specifically, carbon dioxide gas, vitamin E and its derivatives, and plant extracts such as ginger, capsicum tincture, and Sophora flavescens root.

Examples of substances with a moisturizing effect include proteins such as elastin and keratin, their derivatives, their hydrolysates, and their salts, amino acids such as glycine, serine, aparatic acid, glutamic acid, arginine, theanine, and their derivatives, sugars such as sorbitol, erythritol, trehalose, inositol, glucose, sucrose and its derivative, dextrin and its derivative, and honey, D-panthenol and its derivative, sodium lactate, sodium pyrrolidone carboxylate, sodium hyaluronate, mucopolysaccharides, uric acid, phospholipid, ceramide, Coptis root extract, sweet flag extract, Rehmannia root extract, Cnidium rhizome extract, Malva sylvestris extract, horse-chestnut extract, and quince extract.

Examples of substances with hair repairing effect include isopropyl methyl phenol, Ginkgo biloba extract, L-menthol, carpronium chloride, diphenhydramine hydrochloride, tuber fleece flower (Reynoutria multiflora), glycyrrhizin (dipotassium), salicylic acid, dialkylmonoamine derivatives, ginger, cepharanthine, Cnidium rhizome, Swertia herb, Panax rhizome, Panax ginseng, capsicum tincture, Japanese angelica root, trehalose, nicotinic acid/nicotinamide, vitamin E (tocopherol), hinokitiol, placenta extract, and pentadecanoic glyceride.

Substances with a skin conditioning effect include substances used to improve a barrier function or improve rough skin that is, for example, heal wounds. Examples of substances with a skin conditioning effect include ceramides, cholesterols, amine derivatives, caffeines, Celosia argentea extract, shell extract, royal jelly, silk protein and its degradants and derivatives, lactoferrin and its degradants, chondroitin sulfate, mucopolysaccharides such as hyaluronic acid and their salts, collagen, yeast extract, lactic acid bacteria extract, Bifidobacterium extract, fermentation products, Ginkgo biloba extract, barley extract, Swertia herb extract, jujube extract, carrot extract, Arnica extract, turmeric extract, eucalyptus extract, Typha latifolia extract, Saponaria officinalis extract, rosemary extract, glycol extract, citric acid, lactic acid, malic acid, tartaric acid, and succinic acid.

Examples of substances with a relaxing effect include lavender, rosemary, sandalwood, iris, bitter orange, cypress, and orange oil.

These medical agents may be used alone or in combination of two or more.

Examples of cosmetics include lotion, emulsion, serum, cream, cream mask, massage cream, cleansing cream, cleansing gel, face washing foam, sunscreen, styling gel, shampoo, body shampoo, hair setting gel, fragrance, and hair dye. Effects of anti-aging, whitening, peeling, brightening, slimming, moisturizing, hair repairing, hair growing, skin conditioning, relaxing, and UV protection can be obtained from these cosmetics.

Note that these cosmetics may be used alone or in combination of two or more.

(Method of Manufacturing Positive Electrode)

Next, a method of manufacturing the positive electrode is described.

First, the method of producing carbonized bacterial cellulose forming the positive electrode 201 is described.

Figure 6:
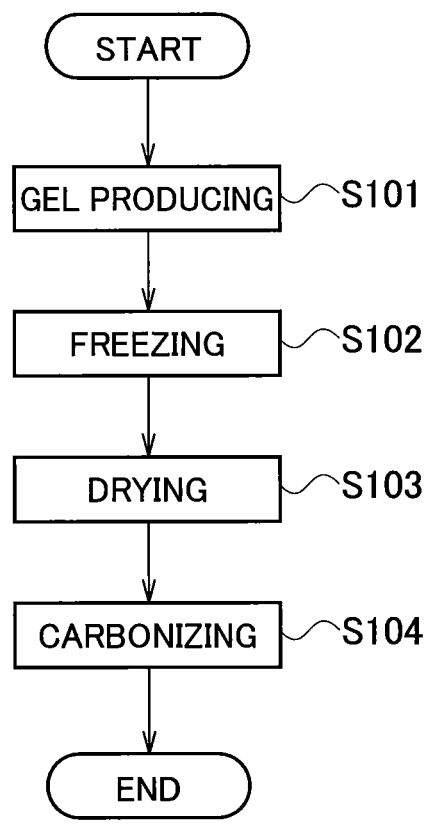
FIG. 6 is a flowchart illustrating a method of producing carbonized bacterial cellulose.

FIG. 6 is a flowchart illustrating a method of producing the carbonized bacterial cellulose.

In a gel producing step of step S101, certain bacteria are made to produce a gel in which nanofibers of cellulose are dispersed. In a freezing step of step S102, the gel produced by the bacteria is frozen to be a frozen body. In a drying step of step S103, the frozen body is dried in vacuum. The bacterial xerogel is obtained by the aforementioned steps. In a carbonizing step of step S104, the bacterial xerogel is carbonized by being heated in a gas atmosphere in which cellulose does not combust. The carbonized bacterial cellulose is thereby obtained.

The gel means a substance in which a dispersion medium loses fluidity due to a three-dimensional network structure of a nano-structure body being a dispersoid and which thereby becomes solid. Specifically, the gel means a dispersion with a shear modulus of $10^2$ to $10^6$ Pa. An aqueous dispersion medium such as water ($H_2O$) may be used as the dispersion medium of the gel. Alternatively, an organic dispersion medium such as carboxylic acid, methanol ($CH_3OH$), ethanol ($C_2H_5OH$), propanol ($C_3H_7OH$), n-butanol, isobutanol, n-butylamine, dodecane, unsaturated fatty acid, ethylene glycol, heptane, hexadecane, isoamyl alcohol, octanol, isopropanol, acetone, or glycerine may be used as the dispersion medium of the gel. Two or more of these media may be mixed.

The gel produced by the bacteria has nanofibers in the nm order (fibrous substance with a diameter of 1 nm to 1 μm and a length 100 times or more the diameter) as a basic structure.

The positive electrode 201 fabricated by using this gel has a high specific surface area. Since the positive electrode 201 of the biological tissue transdermal patch 1 desirably has a high specific surface area, the gel produced by the bacteria is preferably used. Specifically, using the gel produced by the bacteria enables synthesis of the positive electrode 201 with a specific surface area of 300 $m^2/g$ or more.

The bacterial gel has a structure in which fibers are entangled in a coil shape or a mesh shape and has a structure in which nanofibers formed by cultivation of the bacteria branch. Accordingly, the positive electrode 201 fabricated from the bacterial gel can achieve such an excellent elastic property that strain at elastic limit is 50% or more. Thus, the positive electrode 201 fabricated by using the bacterial gel can be improved in adhesion to the biological tissue.

The bacteria may be publicly-known bacteria and examples thereof include acetobacters such as *Acetobacter xylinum* subspecies sucrofermentans, *Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142, and *Acetobacter xylinum* ATCC10821. Moreover, the bacteria may be bacteria produced by cultivating mutants created by subjecting the aforementioned bacteria to mutation processing of a publicly-known method using NTG (nitrosoguanidine) or the like.

In the freezing step, for example, the bacterial gel is housed in an appropriate container such as a test tube and is frozen by cooling the surrounding of the test tube in a coolant such as liquid nitrogen. The method of freezing the bacterial gel is not limited to a particular method as long as the dispersion medium of the gel can be cooled to or below a freezing point and the gel may be cooled with a freezer or the like. Freezing the bacterial gel causes the dispersion medium to lose fluidity and fixes the cellulose which is the dispersoid and the three-dimensional network structure is thereby formed. If the cellulose which is the dispersoid is not fixed by the freezing, the dispersoid aggregates with evaporation of the dispersion medium in the later drying step. Accordingly, a sufficiently-high specific surface area cannot be obtained and fabrication of the positive electrode 201 with high performance is difficult.

The drying step is a step of drying the frozen body obtained in the freezing step and taking out the cellulose, which is the dispersoid maintaining or forming the three-dimensional network structure, from the dispersion medium. In the drying step, the frozen body is dried in vacuum and the frozen dispersion medium sublimates from a solid state. The drying step is performed by, for example, housing the obtained frozen body in an appropriate container such as a flask and vacuuming the inside of the container. Disposing the frozen body in a vacuum atmosphere can lower the sublimation point of the dispersion medium and allows substances which do not sublimate in a normal pressure to sublimate. The degree of vacuum in the drying step varies depending on the used dispersion medium but is not limited to a particular degree of vacuum as long as the dispersion medium sublimates. For example, when water is used as the dispersion medium, the degree of vacuum in which the pressure is 0.06 MPa or less needs to be achieved. However, since heat is absorbed as latent heat of sublimation, the drying takes time. Accordingly, the degree of vacuum of $1.0 \times 10^{-6}$ to $1.0 \times 10^{-2}$ Pa is preferable. Furthermore, the frozen body may be heated with a heater or the like in the drying. In a method in which the frozen body is dried in the atmosphere, the dispersion medium changes from solid to liquid and then from liquid to gas. When the dispersion medium changes to a liquid state, the dispersoid becomes flexible in the dispersion medium and the three-dimensional network structure of cellulose collapses. Accordingly, it is difficult to fabricate elastic carbonized bacterial cellulose in the drying in the atmosphere of atmospheric pressure.

The cellulose which is a component contained in the bacterial gel is not electrically conductive. Accordingly, the carbonizing step of heating and carbonizing the cellulose in an inert gas atmosphere to provide electrically-conductive property to the cellulose is important. The carbonized bacterial cellulose has an electrically-conductive three-dimensional network structure. The carbonized bacterial cellulose has high electrical conductivity, a corrosion-proof property, a high elastic property, and a high specific surface area and is preferable as the positive electrode 201 of the biological tissue transdermal patch 1.

In the carbonizing step, the bacterial xerogel may be baked and carbonized in an inert gas atmosphere at preferably 500° C. to 2000° C., more preferably at 900° C. to 1800° C. Examples of a gas in which cellulose does not combust include inert gases such as nitrogen gas and argon gas. The gas to be used may be a reducing gas such as hydrogen gas and carbon monoxide gas or may be carbon dioxide gas. Carbon dioxide gas or carbon monoxide gas which has an activation effect on a carbon material and by which high activation can be expected is more preferable.

Next, the step of causing the carbonized bacterial cellulose to support the catalyst is described.

Figure 7:
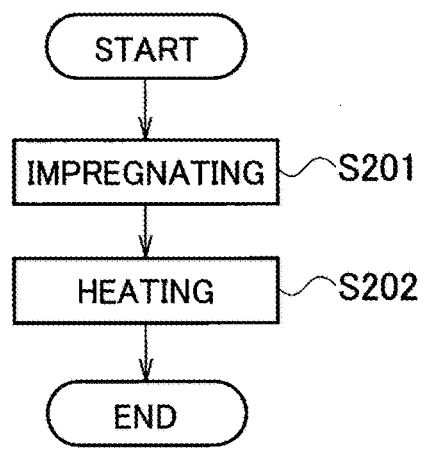
FIG. 7 is a flowchart illustrating a step of causing the carbonized bacterial cellulose to support a catalyst.

FIG. 7 is a flowchart illustrating the step of causing the carbonized bacterial cellulose to support the catalyst.

In an impregnating step of step S201, the carbonized bacterial cellulose obtained in the aforementioned producing method is impregnated with an aqueous solution of a metal salt which is to be a precursor of the catalyst. In a heating step of step S202, the carbonized bacterial cellulose containing the metal salt is heated.

A metal preferable as the metal salt is at least one metal selected from the group including iron, manganese, copper, nickel, silver, gold, platinum, cobalt, ruthenium, molybdenum, titanium, chrome, gallium, praseodymium, aluminum, silicon, and tin. Iron has low environmental load and high electrode performance and is thus preferable.

A conventionally-known method can be used to make the carbonized bacterial cellulose support a transition metal oxide. Examples of such a method include a method in which the carbonized bacterial cellulose is impregnated with an aqueous solution of a transition metal chloride or a transition metal nitrate and subjected to evaporation to dryness and then to hydrothermal synthesis in water at high temperature and high pressure, a precipitation method in which the carbonized bacterial cellulose is impregnated with an aqueous solution of a transition metal chloride or a transition metal nitrate and alkaline aqueous solution is added dropwise, and a sol-gel method in which the carbonized bacterial cellulose is impregnated with a transition metal alkoxide solution and is hydrolyzed. Conditions in these liquid-phase methods are publicly known and these publicly-known conditions may be applied. Since the transition metal oxide can be supported in high dispersion, these liquid-phase methods are desirable.

Since crystallization of the metal oxide supported in the aforementioned liquid-phase methods do not progress in many cases, the metal oxide is amorphous. Crystalline metal oxide can be obtained by heating the amorphous precursor in an inert atmosphere at high temperature of about 500° C. Such crystalline metal oxide has as excellent performance when used as the catalyst of the positive electrode.

Meanwhile, precursor powder obtained by drying the aforementioned amorphous precursor at relatively low temperature of about 100° C. to 200° C. turns into a hydrate with the amorphous state maintained. The hydrate of the metal oxide can be formally expressed as $Me_xO_y\cdot nH_2O$ (where Me denotes the aforementioned metal, x and y denote the numbers of atoms of metal and oxygen contained in a metal oxide molecule, respectively, and n denotes the number of moles of $H_2O$ relative to one mole of the metal oxide). The hydrate of the metal oxide obtained by such low temperature drying may be used as the catalyst.

Since the amorphous metal oxide (hydrate) is hardly sintered, the amorphous metal oxide has a large surface area and has a very small particle diameter of about 30 nm. These characteristics are preferable as the catalyst and an excellent battery performance can be obtained by using this metal oxide.

Although the crystalline metal oxide has high activity as described above, the metal oxide crystallized by being heated at high temperature as described above sometimes has a greatly-reduced surface area. For example, the particle diameter sometimes increases to about 100 nm due to aggregation of particles. Note that this particle diameter (average particle diameter) is a value obtained by observing the particles with a scanning electron microscope (SEM) or the like in a magnified manner to measure the diameters of particles in a 10 μm square (10 μm×10 μm) area and obtaining the average value of the diameters.

Moreover, since particles aggregate particularly in a catalyst formed of a metal oxide heated at high temperature, it is sometimes difficult to add the catalyst to the surface of the carbonized bacterial cellulose in high dispersion. A large amount of the metal oxide sometimes needs to be added into the positive electrode to obtain a sufficient catalyst effect and the fabrication of the catalyst by heating at high temperature is sometimes disadvantageous in terms of cost. In order to solve these problems, the aforementioned amorphous precursor may be dried at relatively low temperature of about 100° C. to 200° C. as described above.

It is possible to process the carbonized bacterial cellulose not supporting the catalyst or the carbonized bacterial cellulose supporting the catalyst obtained in the aforementioned manufacturing method into a plate-shaped body or a sheet and cut the plate-shaped body or the sheet of the carbonized bacterial cellulose into a desired rectangular shape (for example, 30 mm×20 mm) by using a blanking blade, a laser cutter, and the like to form it into the positive electrode 201.

Next, another method of manufacturing the positive electrode is described.

The carbonized bacterial cellulose obtained in the aforementioned manufacturing method is brittle and is sometimes difficult to process into a desired shape. Using the other manufacturing method described below facilitates processing of the carbonized bacterial cellulose into a sheet shape.

Figure 8:
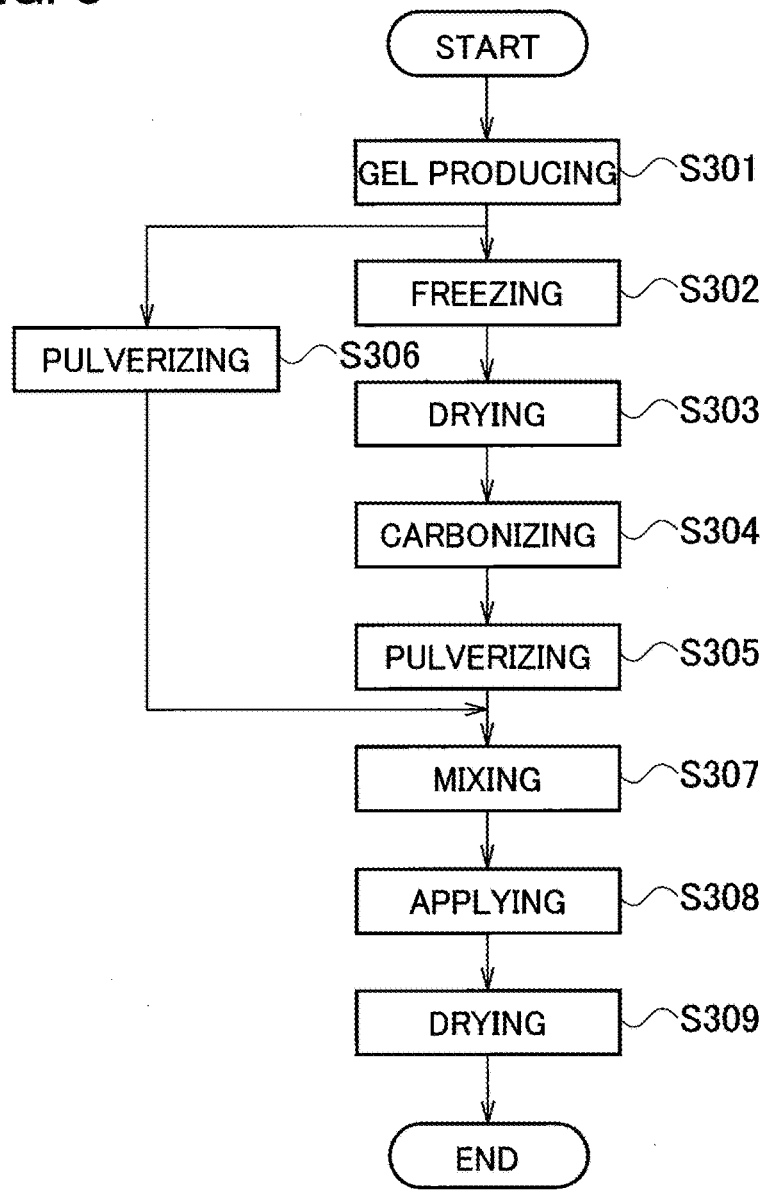
FIG. 8 is a flowchart illustrating another method of manufacturing a positive electrode.

FIG. 8 is a flowchart illustrating the other method of manufacturing the positive electrode 201.

Steps S301 to S304 are the same as the steps in the method of producing the carbonized bacterial cellulose described in FIG. 6. After step S304, the step of causing the carbonized bacterial cellulose to support the catalyst described in FIG. 7 may be performed.

In a pulverizing step of step S305, the carbonized bacterial cellulose obtained in steps S301 to S304 is pulverized. In a pulverizing step of step S306, the bacterial gel obtained in step S301 is pulverized. In a mixing step of step S307, the carbonized bacterial cellulose pulverized in step S305 and the bacterial gel pulverized in step S306 mixed.

In the pulverizing steps, the bacterial gel and the carbonized bacterial cellulose are pulverized into powder or slurry by using, for example, a mixer, a homogenizer, an ultrasonic homogenizer, a high-speed rotation shear mixer, a colloid mill, a roll mill, a high-pressure spray dispersing machine, a rotary ball mill, a vibrating ball mill, a planetary ball mill, or an attritor. In this case, the secondary particle diameter of the bacterial gel and the carbonized bacterial cellulose is preferably 100 nm to 5 mm, more preferably 1 μm to 1 mm. This is because, if the bacterial gel and the carbonized bacterial cellulose are pulverized such that the secondary particle diameter becomes 100 nm or smaller, a bicontinuous structure of the nanofibers breaks. This makes it difficult to obtain sufficient binding force and an electrically-conductive path and electrical resistance increases. If the secondary particle diameter is 5 mm or more, the bacterial gel functioning as a binder is not sufficiently dispersed and this makes it difficult to maintain the positive electrode in a sheet shape.

The carbonized bacterial cellulose has high porosity and low density. Accordingly, when the carbonized bacterial cellulose alone is pulverized, powder of the carbonized bacterial cellulose float in the air during or after the pulverization and handling thereof is thus difficult. Accordingly, it is preferable to impregnate the carbonized bacterial cellulose with a solvent and then pulverize the carbonized bacterial cellulose. The solvent used in this case is not limited to a particular solvent and, for example, an aqueous solvent such as water ($H_2O$) may be used. Alternatively, an organic solvent such as carboxylic acid, methanol ($CH_3OH$), ethanol ($C_2H_5OH$), propanol ($C_3H_7OH$), n-butanol, isobutanol, n-butylamine, dodecane, unsaturated fatty acid, ethylene glycol, heptane, hexadecane, isoamyl alcohol, octanol, isopropanol, acetone, or glycerine may be used as the solvent. Two or more of these solvents may be mixed.

The bacterial gel and the carbonized bacterial cellulose can be simultaneously pulverized. Such a case is preferable because the mixing step can be omitted.

The mixture produced in the aforementioned pulverizing step and mixing step is in a form of slurry. In an applying step of step S308, this mixed slurry is applied to the separator 203, 203A or the electrically-conductive layer 204, 204A. In a drying step of step S309, the applied mixed slurry is dried. The sheet-shaped positive electrode 201 can be processed into a desired shape in the aforementioned steps.

In the applying step, the mixed slurry may applied to either of the separator 203, 203A or the electrically-conductive layer 204, 204A. When the xerogel is used for the separator 203, 203A, the xerogel absorbs the solvent in the application and turns into gel. Accordingly, the mixed slurry is preferably applied to the electrically-conductive layer 204, 204A.

In the drying step, a thermostat chamber, a vacuum drier, an infrared drier, a hot air drier, or a suction drier may be used. Moreover, the solvent can be quickly dried by performing suction filtering with an aspirator or a like.

As another method, the mixed slurry may be dried and formed into a sheet shape and then processed into a desired shape. For example, the obtained sheet-shaped carbonized bacterial cellulose is cut into a desired rectangular shape (for example, 30 mm×20 mm) by using a blanking blade, a laser cutter, and the like to be formed into the positive electrode 201. However, material cost is higher than that in the method of applying the mixed slurry due to scraps or the like generated in the blanking.

The positive electrode 201 may be fabricated by using cellulose nanofiber carbon instead of the carbonized bacterial cellulose. A manufacturing method using the cellulose nanofiber carbon is the same as the manufacturing method using the carbonized bacterial cellulose.

Specifically, as in the manufacturing method of FIG. 6, in the freezing step, a solution containing cellulose nanofiber is frozen to obtain a frozen body. In the drying step, the frozen body is dried in vacuum to obtain a dried body. In the carbonizing step, the dried body is carbonized by being heated in an atmosphere of a gas in which cellulose does not combust. The cellulose nanofiber carbon is thereby obtained. The cellulose nanofiber carbon manufactured in this manufacturing method has a fibrous mesh structure. The cellulose nanofiber carbon has an electrically-conductive three-dimensional network structure and has physical properties, characteristics, and performance equivalent to those of the carbonized bacterial cellulose. The cellulose nanofiber carbon is processed into a plate shape or a sheet and is cut into a desired shape to be formed into the positive electrode 201. Note that, as in the step of FIG. 7, the cellulose nanofiber carbon may be made to support the catalyst.

Moreover, as in the manufacturing method of FIG. 8, the positive electrode 201 may be fabricated by producing slurry from the cellulose nanofiber carbon and applying and drying the slurry. In the pulverizing step, the cellulose nanofiber carbon produced as described above is pulverized. In the mixing step, a cellulose nanofiber solution and the pulverized cellulose nanofiber carbon are mixed. A mixture in a form of slurry is thereby obtained. In the applying step and the drying step, the mixed slurry is applied to the separator 203, 203A or the electrically-conductive layer 204, 204A and dried.

(Method of Manufacturing Negative Electrode)

Next, a method of manufacturing the negative electrode is described.

Figure 9:
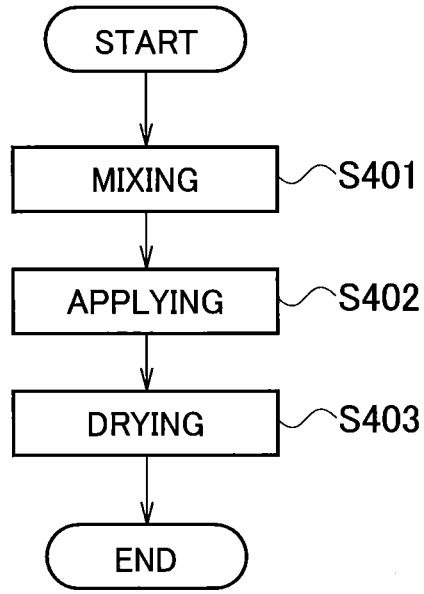
FIG. 9 is a flowchart illustrating a method of manufacturing a negative electrode.

FIG. 9 is a flowchart illustrating the method of manufacturing the negative electrode 202.

In a mixing step of step S401, predetermined metal powder containing magnesium is mixed with a binder and a conductive additive. In an applying step of step S402, mixed slurry obtained by the mixing is applied to the separator 203, 203B or the electrically-conductive layer 204, 204B. In a drying step of step S403, the applied mixed slurry is dried. The negative electrode 202 can be fabricated by the aforementioned steps. The manufacturing method of FIG. 9 can achieve lower material cost than a method of cutting a magnesium foil into a predetermined shape and a thin, flexible negative electrode 202 can be fabricated.

In the mixing step, slurry containing the binder, the conductive additive, and the metal powder containing magnesium is produced by using, for example, a magnetic stirrer, a stirrer, a mixer, a planetary centrifugal mixer, a vacuum mixing-degassing mixer, a mixing apparatus, a homogenizer, an ultrasonic homogenizer, a high-speed rotation shear mixer, a colloid mill, a roll mill, a high-pressure spray disperser, a rotary ball mill, a vibrating ball mill, a planetary ball mill, or an attritor.

The mixed metal powder containing magnesium can be pure magnesium or an alloy mainly containing magnesium. Examples of the alloy mainly containing magnesium include AZ31, AZ31B, AZ61, AZ91, AMX601, AMX602, AZX611, AZX612, AM50, AM60, and LZ91.

A conventional method of synthesizing magnesium powder can be used for synthesis of the metal powder containing magnesium. Examples of the method include a water atomization method, a gas atomization method, a centrifugal atomization method, a melt spinning method, a rotating electrode method, a stamp mill method, a ball mill method, a mechanical alloying method, an oxidation-reduction method, a chloride reduction method, a hydrometallurgy method, an electrolytic method, a carbonyl reaction method, and a hydrogen plasma irradiation method.

The particle diameter of the metal powder containing magnesium is preferably 10 nm to 5 µm, more preferably 20 nm to 2 µm. This is because, if the particles are too large, the particles are less likely to come into contact with each other when the application and the drying are performed and the electric conductivity decreases. If the particles are too small, there is a risk that oxidation reaction progresses and magnesium becomes inactive. In some cases, the oxidation reaction may progress rapidly and cause magnesium metal to combust, thereby leading to fire accidents.

The mixed binder may be any binder which causes the particles to bind with each other after the step of drying the slurry. Substances which contain no fluorine and are used as food additives such as gum arabic, sodium alginate, curdlan, carrageenan, agar, xanthan gum, chitosan, guar gum, konjac powder, cyclodextrin, gelatin, tamarind gum, tara gum, dextrin, starch, pregelatinized starch, pullulan, pectin, egg white, locust bean gum, propylene glycol, glycerin, soybean protein, CMC, cellulose, and bacterial cellulose are preferable. Since the pulverized bacterial cellulose used in the fabrication of the positive electrode 201 has a structure in which the nanofibers are three-dimensionally entangled and this structure firmly binds the metal powder containing magnesium, the pulverized bacterial cellulose is preferable as the binder. Since the bacterial cellulose is a material necessary for the synthesis of the positive electrode 201, the same material can be used for the positive electrode 201 and the negative electrode 202 and this is advantageous in terms of cost.

The mixed conductive additive is preferably, for example, carbonized bacterial cellulose, carbon powder, or an electrically-conductive polymer and the electrically-conductive polymer which has a high binding property with the metal powder containing magnesium is most preferable. Examples of the electrically-conductive polymer include polyacetylene which is an aliphatic conjugated system, poly(p-phenylene) which is an aromatic conjugated system, and poly (p-phenylene vinylene) and poly(thienylene vinylene) which are mixed conjugated systems, polypyrrole, polythiophene, and polyethylenedioxythiophene (PEDOT) which are heterocyclic conjugated systems, polyaniline which is a heteroatom containing conjugated system, polyacene and polyfluorene which are double-chain conjugated systems, and graphene which is a two-dimensional conjugated system. PEDOT with excellent electrical-conductivity and excellent environmental stability in a conductive state is preferable.

In the mixing step, solvent is preferably added in addition to the binder, the conductive additive, and the metal powder containing magnesium. The solvent is not limited to a particular solvent and, for example, an aqueous solvent such as water ($H_2O$) may be used. Alternatively, organic solvent such as carboxylic acid, methanol ($CH_3OH$), ethanol ($C_2H_5OH$), propanol ($C_3H_7OH$), n-butanol, isobutanol, n-butylamine, dodecane, unsaturated fatty acid, ethylene glycol, heptane, hexadecane, isoamyl alcohol, octanol, isopropanol, acetone, and glycerine may be used as the solvent. Two or more of these solvents may be mixed.

In the applying step, the mixed slurry may be applied to either of the separator 203, 203B or the electrically-conductive layer 204, 204B. The mixed slurry is preferably applied to the electrically-conductive layer 204, 204B as in the positive electrode 201.

When both of the slurry for the positive electrode and the slurry for the negative electrode are applied to the electrically-conductive layer 204, the drying step may be performed after the application of both of the slurry for the positive electrode and the slurry for the negative electrode to the electrically-conductive layer 204.

The negative electrode 202 may be formed in a publicly-known method instead of the aforementioned manufacturing method. For example, the negative electrode 202 is fabricated by shaping a metal magnesium foil into a predetermined shape.

EXAMPLES AND EVALUATION RESULTS

Next, description is given of examples varying in the configuration of the battery part 2, the materials of the elements in the battery part 2, and the manufacturing methods and of evaluation results of these examples.

Example 1

Figure 10:
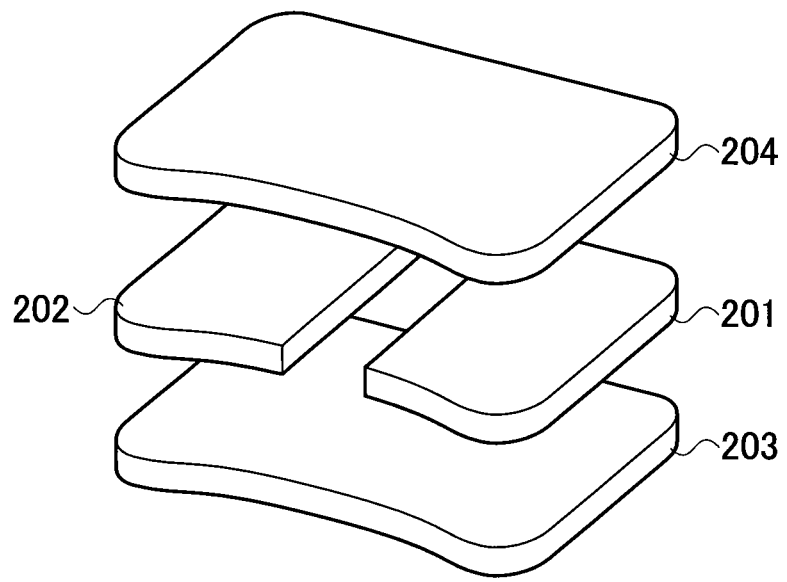
FIG. 10 is an exploded perspective view of the battery part in Examples 1 and 6.
Figure 11:
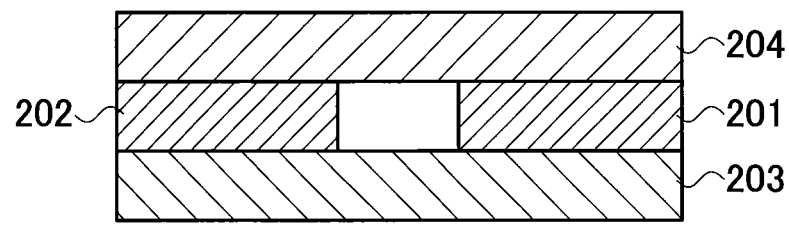
FIG. 11 is a cross-sectional view of the battery part in Examples 1 and 6.

FIG. 10 is an exploded perspective view of the battery part 2 in Example 1. FIG. 11 is a cross-sectional view of the battery part 2 in Example 1.

The battery part 2 in Example 1 included the positive electrode 201, the negative electrode 202, the separator 203, and the electrically-conductive layer 204. In Example 1, the carbonized bacterial cellulose was used for the positive electrode 201. Preparation of the battery part 2 in Example 1 is described below.

The carbonized bacterial cellulose used in the positive electrode 201 was obtained in the following method.

Nata de coco (manufactured by Fujicco) which was a bacteria cellulose gel produced by *Acetobacter xylinum* being acetobacter was used as the bacterial gel and the bacterial gel was immersed in liquid nitrogen for 30 minutes in a styrene foam box to be completely frozen. After the bacterial gel was completely frozen, the frozen bacterial gel was taken out and put on a petri dish and was dried in vacuum of 10 Pa or less by using a freeze dryer (manufactured by Tokyo Rikakikai Co, Ltd) to obtain a bacterial xerogel. After the drying in vacuum, the bacterial xerogel was carbonized by being baked at 1200° C. for two hours in a nitrogen atmosphere and the carbonized bacterial cellulose was obtained.

XRD measurement, SEM observation, porosity measurement, tensile test, and BET specific surface area measurement were performed to evaluate the obtained carbonized bacterial cellulose. It was confirmed in the XRD measurement that the carbonized bacterial cellulose was a carbon (C, PDF card No. 01-071-4630) single-phase material. The PDF card No. is a card number of PDF (Powder Diffraction File) which is a database collected by International Centre for Diffraction Data (ICDD). It was confirmed in the SEM observation that the carbonized bacterial cellulose was a bicontinuous body in which nanofibers with a diameter of 20 nm were continuously connected. The BET specific surface area of the carbonized bacterial cellulose was measured by using a BET apparatus and was 830 $m^2/g$. The porosity of the carbonized bacterial cellulose was measured by performing mercury intrusion porosimetry and was 99% or more. The porosity was calculated from a pore size distribution of the carbonized bacterial cellulose obtained by the mercury intrusion porosimetry with pores modeled as cylindrical shapes. It was confirmed from the results of the tensile test that, when strain of 80% was applied by tensile stress, the tensile stress did not exceed the elastic region and the carbonized bacterial cellulose returned to its shape before the application of the stress. Thus, it was found that the bacterial cellulose had an excellent elastic property also after being carbonized.

The positive electrode 201 was prepared by cutting out the obtained carbonized bacterial cellulose into a rectangular shape with a size of 30 mm×20 mm by using a blanking blade, a laser cutter, and the like.

The negative electrode 202 was prepared by cutting out a commercially-available metal magnesium foil (thickness: 200 μm. manufactured by Nilaco Corporation) into a rectangular shape with a size of 30 mm×20 mm by using a blanking blade, a laser cutter, and the like.

The separator 203 was prepared by cutting out a commercially-available cellulose cotton (BEMCOT, manufactured by Asahi Kasei Corporation) into a rectangular shape with a size of 30 mm×50 mm by using a blanking blade, a laser cutter, and the like.

The electrically-conductive layer 204 was prepared by cutting out a commercially-available carbon cloth (manufactured by TORAY industries, Inc.) into a rectangular shape with a size of 30 mm×50 mm by using a blanking blade, a laser cutter, and the like.

The battery part 2 was prepared by using the aforementioned elements as follows. First, the positive electrode 201 and the negative electrode 202 were laid on the electrically-conductive layer 204 and were sandwiched between the electrically-conductive layer 204 and the separator 203. In this case, the positive electrode 201 and the negative electrode 202 were arranged out of contact with each other. Then, portions 1 mm inside outer peripheries of the positive electrode 201 and the negative electrode 202 were sewed by using a sewing machine to pressure-bond these elements to one another and the battery part 2 was thus obtained.

Figure 12:
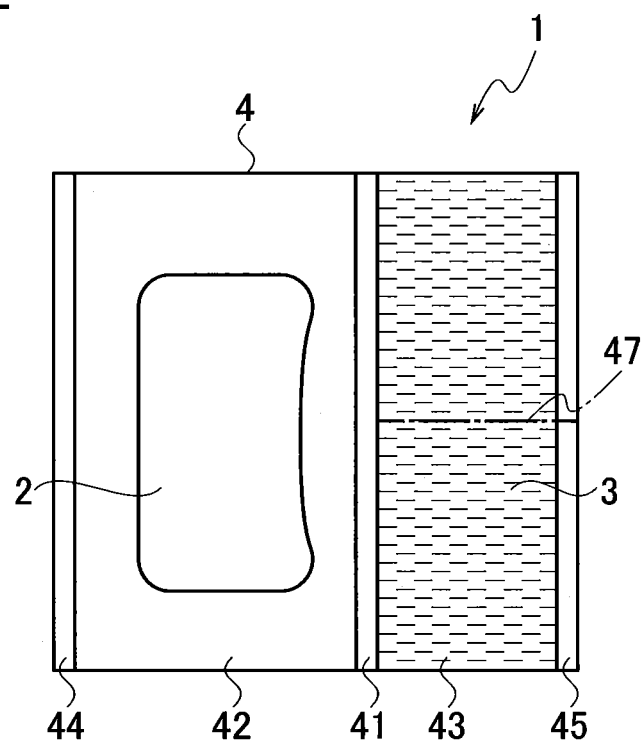
FIG. 12 is a plan view illustrating a configuration of the biological tissue transdermal patch in Example 1.

FIG. 12 is a plan view illustrating a configuration of the biological tissue transdermal patch 1 in Example 1. The biological tissue transdermal patch 1 illustrated in FIG. 12 has the same configuration as that illustrated in FIG. 1 and includes the battery part 2 and the active ingredient 3 which are housed in the plastic pack 4 while being isolated from each other.

The active ingredient 3 was prepared as follows. A carbonate aqueous solution with pH of 8.8 and an L-ascorbic acid (vitamin C) aqueous solution with concentration of 100 μmol/ml were mixed such that a mixture with pH of about 7.4 was prepared. Although the L-ascorbic acid was used as the active ingredient in Example 1, the active ingredient is not limited to this.

The battery part 2 and the active ingredient 3 were housed in the plastic pack 4 while being isolated from each other as follows. First, the battery part 2 was inserted deep into a 10 cm×10 cm polyethylene film pack (manufactured by Nihon Matai Co., Ltd.) with one unsealed side. Then, thermal sealing was performed along a portion 5 cm from a deep end to form the partition wall 41 and the battery part 2 was thereby enclosed. Thereafter, the active ingredient 3 was injected from an opening portion of the plastic pack 4 by using a vacuum liquid injection device (manufactured by Fine flow Inc.) and thermal sealing was performed on the opening portion.

In order to check the storage performance of the biological tissue transdermal patch 1, the biological tissue transdermal patch 1 in which the battery part 2 and the active ingredient 3 were enclosed in the plastic pack 4 was stored for one week in a dark room in which the room temperature was maintained at 25° C., and then used by starting the battery reaction.

First, the active ingredient storage 43 in which the active ingredient 3 was enclosed was folded in half at a folding line 47, and pressure was applied to the active ingredient storage 43 with the finger to break the partition wall 41 and make the active ingredient 3 sufficiently soak into the battery part 2 to start the battery reaction. Making the active ingredient 3 soak into the battery part 2 causes the active ingredient 3 to work also as electrolyte and the battery reaction starts. After checking that the separator 203 of the battery part 2 was soaked with the active ingredient 3, one end 44 of the plastic pack 4 enclosing the battery part 2 was torn with the hands and the battery part 2 was taken out.

Figure 13:
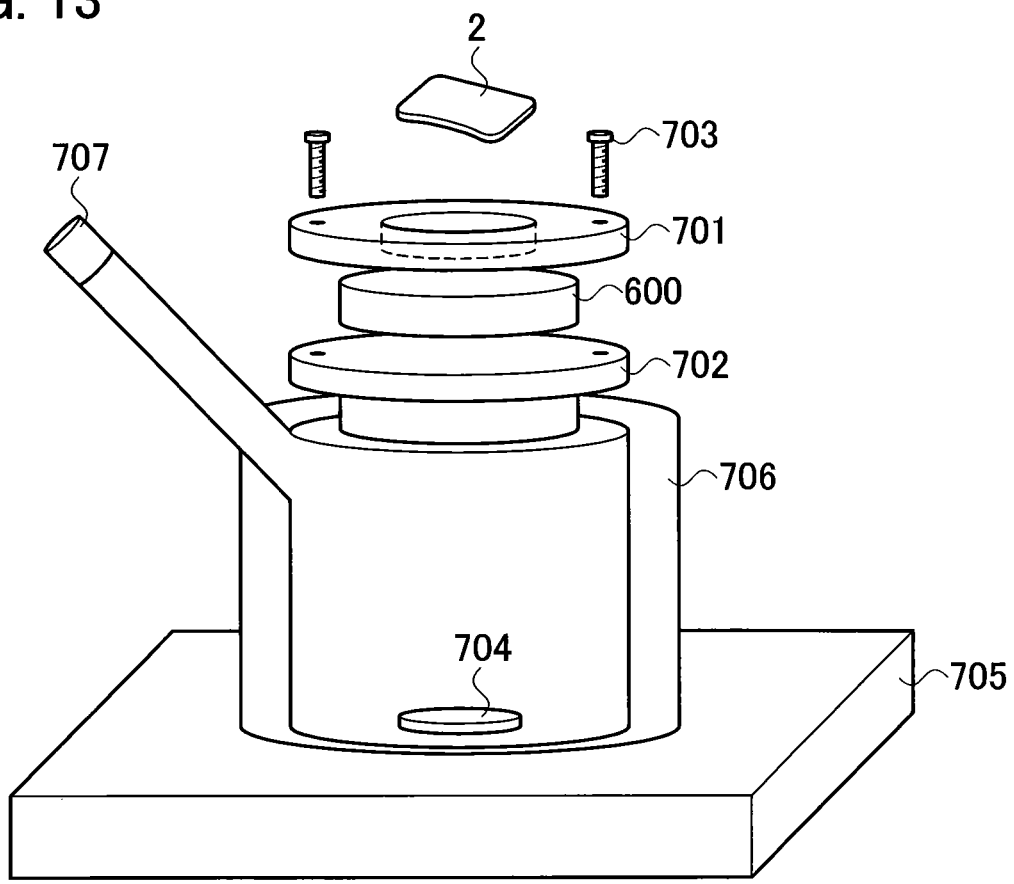
FIG. 13 is a view illustrating a configuration of a test apparatus.

In the evaluation test, the taken-out battery part 2 was disposed on a test apparatus illustrated in FIG. 13 to check a skin permeability of the active ingredient 3 through a test piece (rat skin).

The test apparatus illustrated in FIG. 13 included a donor portion 701 and a receiver portion 702. The test apparatus was used such that a test piece 600 was sandwiched between the donor portion 701 and the receiver portion 702 and was fixed with fasteners 703. Plastic, metal, glass, ceramics, and the like can be used as the materials of the donor portion 701 and the receiver portion 702. In this case, Teflon (registered trademark) was used for the donor portion 701 and glass was used for the receiver portion 702. The receiver portion 702 was filled with an aqueous solution whose pH was adjusted to 7.4 with a phosphate buffer solution and which was supplied from a sampling port 707. Water with constant temperature of 35° C. was circulated in a jacket portion 706 included in the test apparatus. A stir bar 704 was put into the receiver portion 702 and the solution was gently stirred with a magnetic stirrer 705.

The test piece 600 was obtained by anesthetizing a rat fixed on the back with pentobarbital, removing the skin of the abdomen, removing fat from the skin, and hydrating the skin with a phosphate buffer solution with pH of 7.4 for 30 minutes. In fixing of the test piece 600 to the test apparatus, the stratum corneum side was arranged on the donor portion 701 side and the dermis side was arranged on the receiver portion 702 side.

Figure 14:
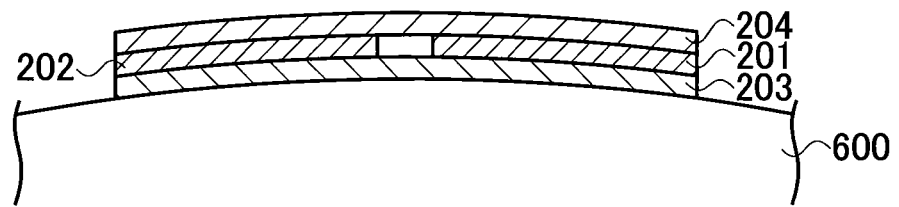
FIG. 14 is a view illustrating how the battery part is disposed on the test apparatus.

As illustrated in FIG. 14, the test piece 600 to which the battery part 2 starting the battery reaction was attached was installed to come into contact with the phosphate buffer solution filling the lower portion of the receiver portion 702. The active ingredient 3 seeped into the phosphate buffer solution through the test piece 600. The solution was taken out from the donor portion 701 at regular time intervals and the cumulative permeation amount through the test piece 600 was calculated.

The concentration measurement was performed by using a high-performance liquid chromatography (manufactured by Agilent Technologies, Inc.). Agilent Poroshell 120 EC-C18 with a size of 4.6×100 mm was used as a column. A solution obtained by adjusting pH of 20 mmol of dihydrogen phosphate buffer ($KH_2PO_4$) to 2.5 with o-phosphoric acid and 60% methanol/40% acetonitrile were used as a mobile phase. The measurement was performed at a flow rate of 1.5 mL/min and the detection wavelength was 243.5 nm.

Note that the measurement results of Example 1 are described later together with the measurement results of Comparative Example 1 to be described later.

Comparative Example 1

Figure 15:
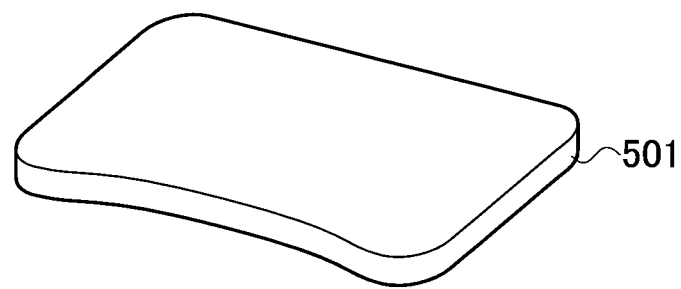
FIG. 15 is a perspective view of the biological tissue transdermal patch in Comparative Example 1.
Figure 16:
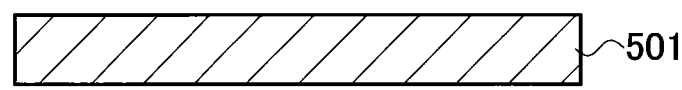
FIG. 16 is a cross-sectional view of the biological tissue transdermal patch in Comparative Example 1.

FIG. 15 is a perspective view of a biological tissue transdermal patch in Comparative Example 1. FIG. 16 is a cross-sectional view of Comparative Example 1.

A biological tissue transdermal patch 501 using only the same separator and the active ingredient as those in Example 1 was fabricated as a comparative example including no battery part.

The biological tissue transdermal patch 501 was prepared by cutting out a commercially-available cellulose cotton (BEMCOT, manufactured by Asahi Kasei Corporation) into a rectangular shape with a size of 30 mm×50 mm by using a blanking blade, a laser cutter, and the like as in Example 1.

The biological tissue transdermal patch 501 was impregnated with the same active ingredient as that in Example 1. As in Example 1, the active ingredient was prepared by mixing the carbonate aqueous solution with pH of 8.8 and the L-ascorbic acid (vitamin C) aqueous solution with concentration of 100 μmol/ml such that a mixture with pH of about 7.4 was prepared.

Figure 17:
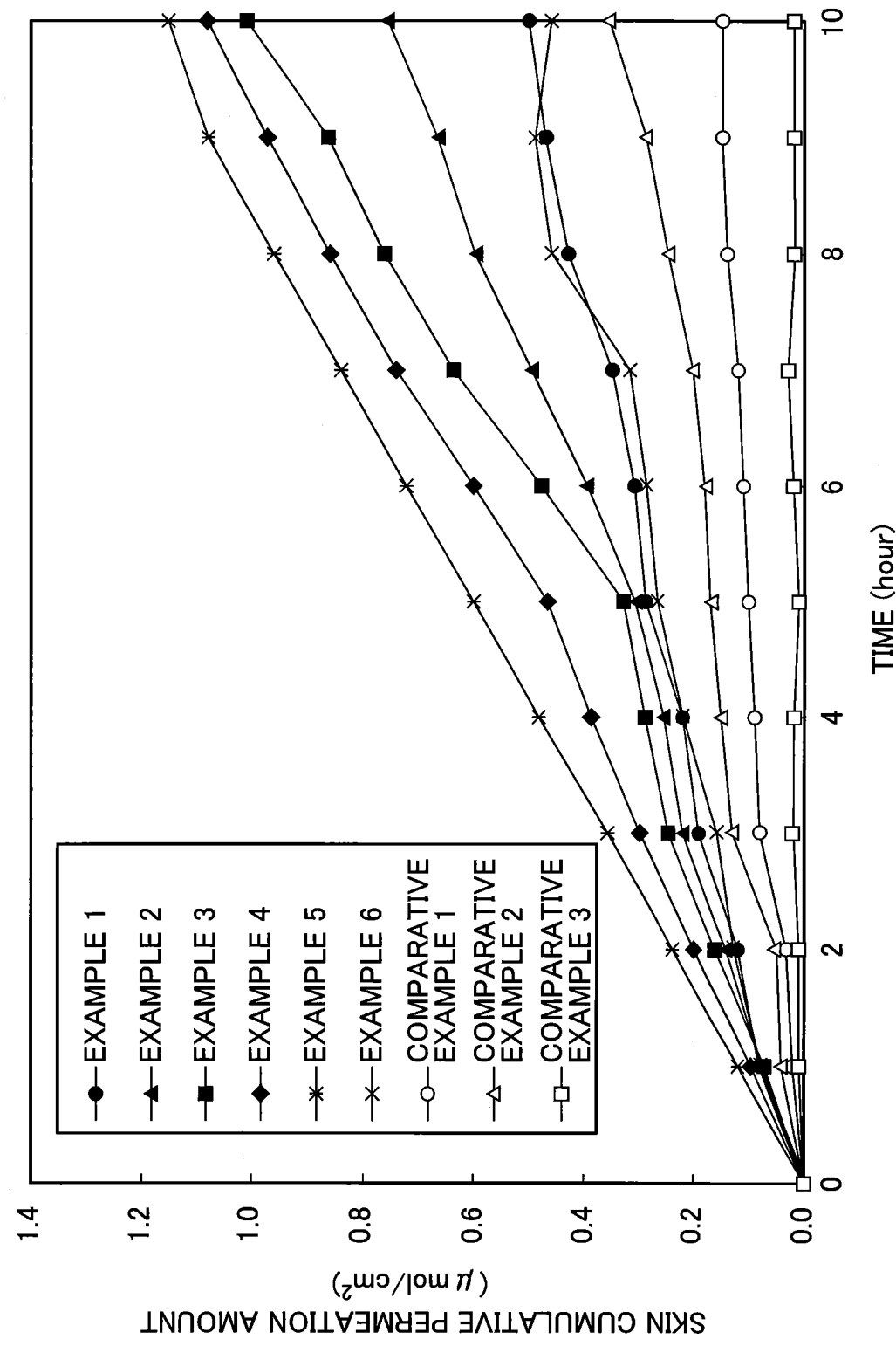
FIG. 17 is a graph illustrating measurement results.

FIG. 17 illustrates the measurement results of Example 1 and Comparative Example 1. Note that the measurement results of Examples 2 to 6 and Comparative Examples 2 and 3 to be described later are also illustrated in FIG. 17.

As apparent from the measurement results illustrated in FIG. 17, in Example 1, the cumulative permeation amount of L-ascorbic acid increased over time. It is assumed that this is because the ionized L-ascorbic acid was introduced into the biological tissue with the movement of the hydroxide ions into the biological tissue associated with the battery reaction.

Meanwhile, no great change in the cumulative permeation amount of L-ascorbic acid was observed in Comparative Example 1.

Examples 2 to 6 and Comparative Examples 2 and 3 are described below one by one.

Example 2

Figure 18:
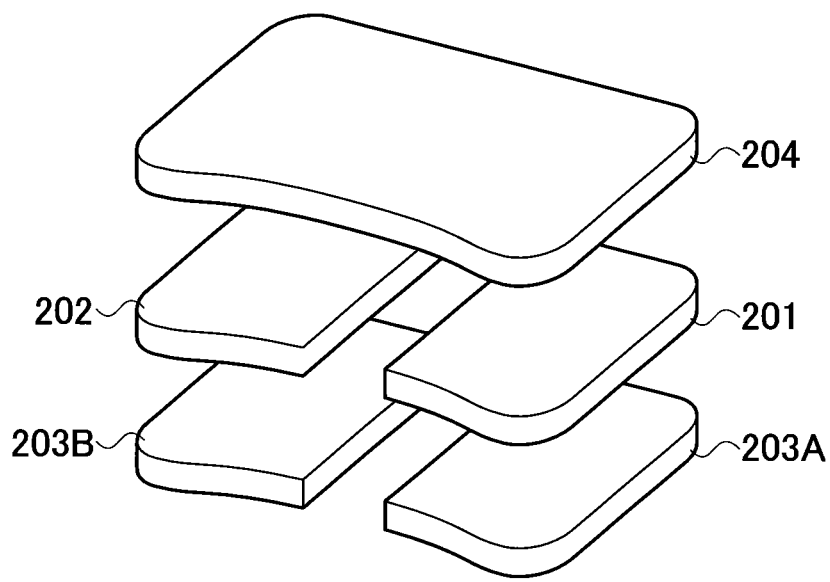
FIG. 18 is an exploded perspective view of the battery part in Example 2.
Figure 19:
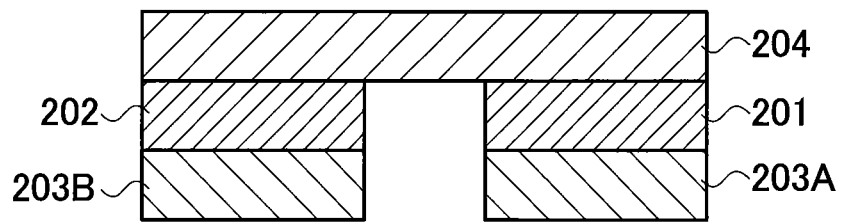
FIG. 19 is a cross-sectional view of the battery part in Example 2.

FIG. 18 is an exploded perspective view of the battery part 2 in Example 2. FIG. 19 is a cross-sectional view of the battery part 2 in Example 2.

Example 2 was different from Example 1 in that the battery part 2 included the positive electrode separator 203A and the negative electrode separator 203B arranged away from each other. The separator 203 of Example 1 was cut into two sheets with a rectangular shape with a size of 30 mm×20 mm by using a blanking blade, a laser cutter, and the like to be used as the positive electrode separator 203A and the negative electrode separator 203B.

The manufacturing method, the test apparatus, and the evaluation method of the biological tissue transdermal patch 1 were the same as those in Example 1.

It can be found from the measurement results illustrated in FIG. 17 that the cumulative permeation amount of L-ascorbic acid at each time in Example 2 is greater than those in Example 1 and Comparative Example 1. In Example 1, ions move not only via the biological tissue but also via the separator 203 and the effect of the ion introduction was reduced. In Example 2, the separator was divided into the positive electrode separator 203A and the negative electrode separator 203B. This promoted the movement of the ions via the biological tissue and the effect of the ion introduction was increased.

Example 3

Figure 20:
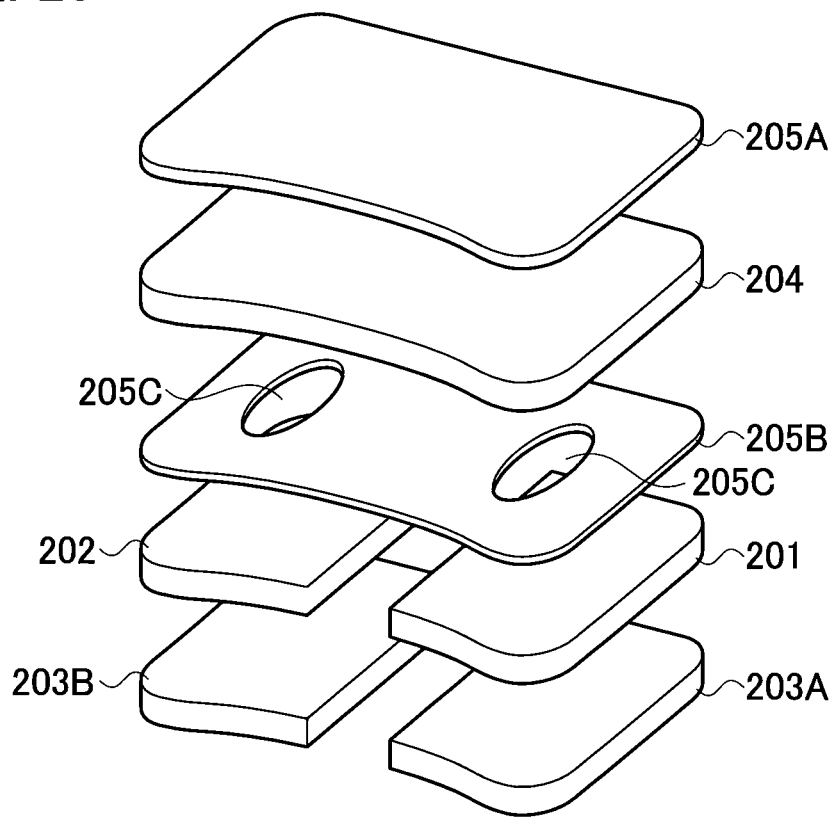
FIG. 20 is an exploded perspective view of the battery part in Examples 3 to 5.
Figure 21:
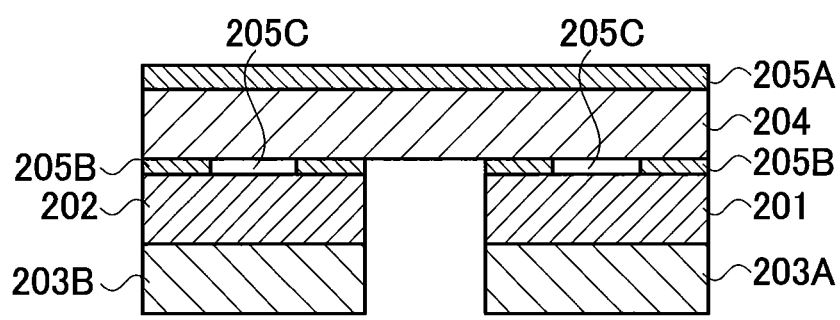
FIG. 21 is a cross-sectional view of the battery part in Examples 3 to 5.

FIG. 20 is an exploded perspective view of the battery part 2 in Example 3. FIG. 21 is a cross-sectional view of the battery part 2 in Example 3.

Example 3 was different from Example 2 in that the electrically-conductive layer 204 was laminated with a plastic film. Specifically, a polyethylene film (manufactured by Thermo K.K.) was cut into two sheets with a rectangular shape with a size of 34 mm×54 mm by using a blanking blade, a laser cutter, and the like and one of the two sheets was used as an upper surface water repelling layer 205A while the other was used as a contact surface water repelling layer 205B. Circular contact portions 205C with a diameter of 10 mm were provided in the polyethylene film of the contact surface water repelling layer 205B by using a blanking blade, a laser cutter, and the like and the electrically-conductive layer 204 was thereby made to come into contact with the positive electrode 201 and the negative electrode 202. The electrically-conductive layer 204 was sandwiched between the upper surface water repelling layer 205A and the contact surface water repelling layer 205B and subjected to thermal sealing to be made water-repellent.

It can be found from the measurement results illustrated in FIG. 17 that the cumulative permeation amount of L-ascorbic acid at each time in Example 3 is greater than those in Examples 1 and 2 and Comparative Example 1. In Example 2, the electrically-conductive layer 204 absorbed the active ingredient 3 and the ion movement via the electrically-conductive layer 204 also occurred. This reduced the effect of the ion introduction. In Example 3, making the electrically-conductive layer 204 water repellent reduced the absorption of the active ingredient 3 by the electrically-conductive layer 204 and promoted the ion movement via the biological tissue.

Example 4

A configuration of the battery part 2 in Example 4 was the same that in Example 3.

Example 4 was different from Example 3 in that a bacterial xerogel was used for the positive electrode separator 203A and the negative electrode separator 203B, instead of the cellulose cotton.

The bacterial xerogel was synthesized in the same synthesizing method as that in Example 1. The bacterial xerogel was cut into two sheets with a rectangular shape with a size of 30 mm×20 mm by using a blanking blade, a laser cutter, and the like and the two sheets were used respectively as the positive electrode separator 203A and the negative electrode separator 203B.

It can be found from the measurement results illustrated in FIG. 17 that the cumulative permeation amount of L-ascorbic acid at each time in Example 4 is greater than those in Examples 1 to 3 and Comparative Example 1. In Example 4, the performance of the separator absorbing the active ingredient 3 was improved by using the bacterial xerogel for the separator. Moreover, after the bacterial xerogel absorbed the active ingredient 3, the bacterial xerogel had excellent flexibility. The adhesion between the biological tissue and the battery part 2 was thereby improved.

Example 5

A configuration of the battery part 2 in Example 5 was the same as those in Examples 3 and 4. Example 5 was the same as Example 4 in that the bacterial xerogel was used for the positive electrode separator 203A and the negative electrode separator 203B.

Example 5 was different from Example 4 in that the manufacturing method of FIGS. 8 and 9 was used and the positive electrode 201 and the negative electrode 202 were fabricated by application onto the electrically-conductive layer 204.

The method of fabricating the positive electrode 201 in Example 5 is described. The bacterial gel and the carbonized bacterial cellulose were fabricated as in Example 1. In the pulverizing step and the mixing step, the carbonized bacterial cellulose was impregnated with water and then the bacterial gel and the carbonized bacterial cellulose were stirred at a weight ratio of 1:1 in a homogenizer (manufactured by SMT CO., LTD.) for 12 hours. In the applying step, the slurry for the positive electrode obtained in the mixing step was applied onto the electrically-conductive layer 204 made water-repellent, in an area of 30 mm×20 mm to a thickness of 3 mm by using a squeegee.

The method of fabricating the negative electrode 202 in Example 5 is described. A flame-resistant magnesium AZX612 (manufactured by Gonda Metal Industry Co., Ltd.) containing 1 wt % of zinc, 2 wt % of calcium, 6 wt % of aluminum in magnesium was used for the negative electrode 202. The flame-resistant magnesium AZX612 was irradiated with hydrogen plasma by using a metal nano-particle manufacturing apparatus (manufactured by Atto Tech) and nano-particles of flame-resistant magnesium AZX612 were synthesized. These nano-particles were observed with a SEM and it was confirmed that the average particle diameter is about 100 nm. Moreover, it was confirmed from results of ICP atomic emission spectrometry that no composition change occurred when the flame-resistant magnesium AZX612 was formed into particles.

A bacterial gel was used as a binder of the negative electrode 202. The bacterial gel was fabricated as in Example 1. The bacterial gel was stirred in a homogenizer (manufactured by SMT CO., LTD.) for 12 hours and the bacterial gel in a form of slurry was obtained.

An aqueous dispersion including a mixture of polyethylenedioxythiophene and polyanion poly(styrenesulfonate) (5.0 wt %, Orgacon EL-P-5015, manufactured by Sigma-Aldrich Corporation) was used as the conductive additive of the negative electrode 202.

In the mixing step, the metal powder containing magnesium, the bacterial gel in a form of slurry, and the aforementioned conductive additive were stirred for 24 hours by using a ball mill.

In the applying step, the slurry for the negative electrode obtained in the mixing step was applied onto the electrically-conductive layer 204 to which the slurry for the positive electrode was applied, in an area of 30 mm×20 mm to a thickness of 3 mm by using a squeegee.

The electrically-conductive layer 204 to which the slurry for the positive electrode and the slurry for the negative electrode were applied was dried at 60° C. for 24 hours by using a thermostat chamber and the positive electrode 201 and the negative electrode 202 were obtained.

The positive electrode separator 203A and the negative electrode separator 203B were fabricated and press-bonded by using a sewing machine as in Example 4 and the battery part 2 was fabricated.

It can be found from the measurement results illustrated in FIG. 17 that the cumulative permeation amount of L-ascorbic acid at each time in Example 5 is greater than those in Examples 1 to 4 and Comparative Example 1. In Example 5, since the positive electrode 201 and the negative electrode 202 were fabricated by application to the electrically-conductive layer 204, the adhesion force of the electrodes 201 and 202 to the electrically-conductive layer 204 was great. This reduced the resistance value and the ion introduction due to the battery reaction was promoted.

Example 6

A configuration of the battery part 2 in Example 6 was the same that in Example 1. Example 6 was different from Example 1 in that cellulose nanofiber carbon was used for the positive electrode 201 instead of the carbonized bacterial cellulose.

The cellulose nanofiber carbon used for the positive electrode 201 was obtained in the following method.

First, cellulose nanofiber (manufactured By Nippon Paper Industries Co., Ltd.) was used and 1 g of cellulose nanofiber and 10 g of pure water were stirred in a homogenizer (manufactured by SMT CO., LTD.) for 12 hours. A cellulose nanofiber solution in which the cellulose nanofibers were dispersed was thereby obtained.

A test tube containing the cellulose nanofiber solution was immersed in liquid nitrogen for 30 minutes and the cellulose nanofiber solution was completely frozen. The frozen cellulose nanofiber solution was taken out on a petri dish and was dried in vacuum of 10 Pa or less by using a freeze dryer (manufactured by Tokyo Rikakikai Co, Ltd) to obtain a dried body of cellulose nanofiber. After the drying in vacuum, the cellulose nanofiber was carbonized by being baked at 600° C. for two hours in a nitrogen atmosphere and the cellulose nanofiber carbon was obtained.

It was confirmed in the XRD measurement that the cellulose nanofiber carbon was a carbon (C, PDF card No. 01-071-4630) single-phase material. It was confirmed in the SEM observation that the cellulose nanofiber carbon was a bicontinuous body in which nanofibers with a diameter of 70 nm were continuously connected. The BET specific surface area of the cellulose nanofiber carbon was measured by using a BET apparatus and was 690 m$^2$/g. The porosity of the cellulose nanofiber carbon was measured by performing mercury intrusion porosimetry and was 99% or more. It was confirmed from the results of the tensile test that, when strain of 30% was applied by tensile stress, the tensile stress did not exceed the elastic region and the cellulose nanofiber carbon returned to its shape before the application of the stress. Thus, it was found that the cellulose nanofiber had an excellent elastic property also after being carbonized.

The manufacturing method, the test apparatus, and the evaluation method of the biological tissue transdermal patch 1 were the same as those in Example 1.

It can be found from the measurement results illustrated in FIG. 17 that the cumulative permeation amount of L-ascorbic acid at each time in Example 6 is greater than that in Comparative Example 1. Moreover, the cumulative permeation amount of L-ascorbic acid at each time in Example 6 is about the same as that in Example 1. This is because the cellulose nanofiber carbon used for the positive electrode 201 had an excellent specific surface area like the carbonized bacterial cellulose and the fibrous mesh structure of the cellulose nanofiber carbon suppressed battery overvoltage and promoted the ion introduction.

Comparative Example 2

A structure of the battery part 2 in Comparative Example 2 was the same as that in Example 1. Comparative Example 2 was different from Example 1 in that carbon (Ketjenblack EC600JD) publicly-known to be used for an electrode of a cathode in a general magnesium-air battery was used for the positive electrode. Specifically, Ketjenblack powder (manufactured by Lion Corporation) and polytetrafluoroethylene (PTFE) powder (manufactured by Daikin Industries, Ltd.) were sufficiently pulverized and mixed in a weight ratio of 50:30:20 by using a mortar machine and subjected to roll forming to be fabricated into a sheet-shaped electrode with thickness of 0.5 mm. The sheet-shaped electrode was cut into a size of 30 mm×20 mm and the positive electrode of Comparative Example 2 was obtained.

The manufacturing method, the test apparatus, and the evaluation method of the biological tissue transdermal patch 1 were the same as those in Example 1.

It can be found from the measurement results illustrated in FIG. 17 that the cumulative permeation amount of L-ascorbic acid at each time in Comparative Example 2 was smaller than those in Examples 1 to 6. Moreover, the positive electrode of Comparative Example 2 was observed after the measurement and it was confirmed that part of the positive electrode collapsed and spots due to carbon powder was formed on the biological tissue.

Comparative Example 3

Comparative Example 3 was an example in which the battery part 2 and the active ingredient 3 in Example 1 were stored in contact with each other. Specifically, in Comparative Example 3, after the biological tissue transdermal patch 1 was fabricated as in Example 1, the partition wall 41 was broken to cause the active ingredient 3 to sufficiently soak into the battery part 2 and then the biological tissue transdermal patch 1 was stored in a dark room in which the room temperature was maintained at 25° C. for one week. Then, the battery part 2 was taken out and evaluated as in Example 1.

It can be found from the measurement results illustrated in FIG. 17 that that the cumulative permeation amount of L-ascorbic acid at each time in Comparative Example 3 is smaller than those in Examples 1 to 6 and Comparative Examples 1 and 2. In Comparative Example 3, since the active ingredient 3 was stored in a state soaking into the battery part 2, deterioration of the battery due to self-discharge, corrosion of the negative electrode, a change in the property of the active ingredient 3, and the like have occurred.

Next, description is given of examples of the battery part 2 in which the electrically-conductive layer is divided into the positive electrode electrically-conductive layer and the negative electrode electrically-conductive layer and of evaluation results of these examples.

Example 7

Figure 22:
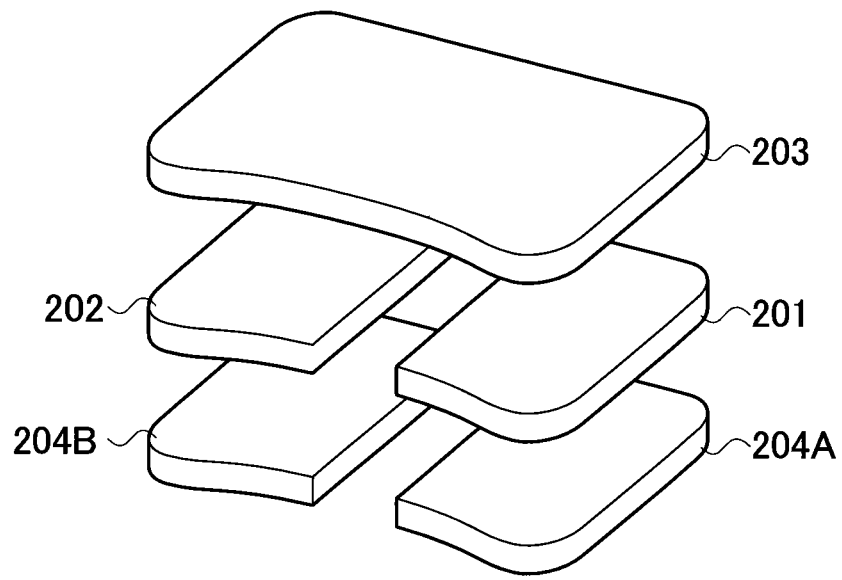
FIG. 22 is an exploded perspective view of the battery part in Examples 7 and 8.
Figure 23:
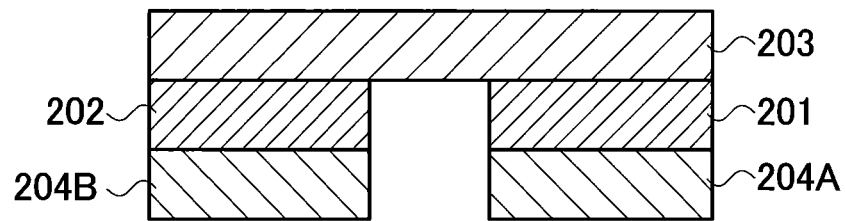
FIG. 23 is a cross-sectional view of the battery part in Examples 7 and 8.

FIG. 22 is an exploded perspective view of the battery part 2 in Example 7. FIG. 23 is a cross-sectional view of the battery part 2 in Example 7.

Example 7 was different from Example 1 in that the battery part 2 included the positive electrode electrically-conductive layer 204A and the negative electrode electrically-conductive layer 204B arranged away from each other. The electrically-conductive layer 204 of Example 1 was cut into two sheets with a rectangular shape with a size of 30 mm×20 mm by using a blanking blade, a laser cutter, and the like to be used as the positive electrode electrically-conductive layer 204A and the negative electrode electrically-conductive layer 204B.

The manufacturing method, the test apparatus, and the evaluation method of the biological tissue transdermal patch 1 were the same as those in Example 1.

Figure 24:
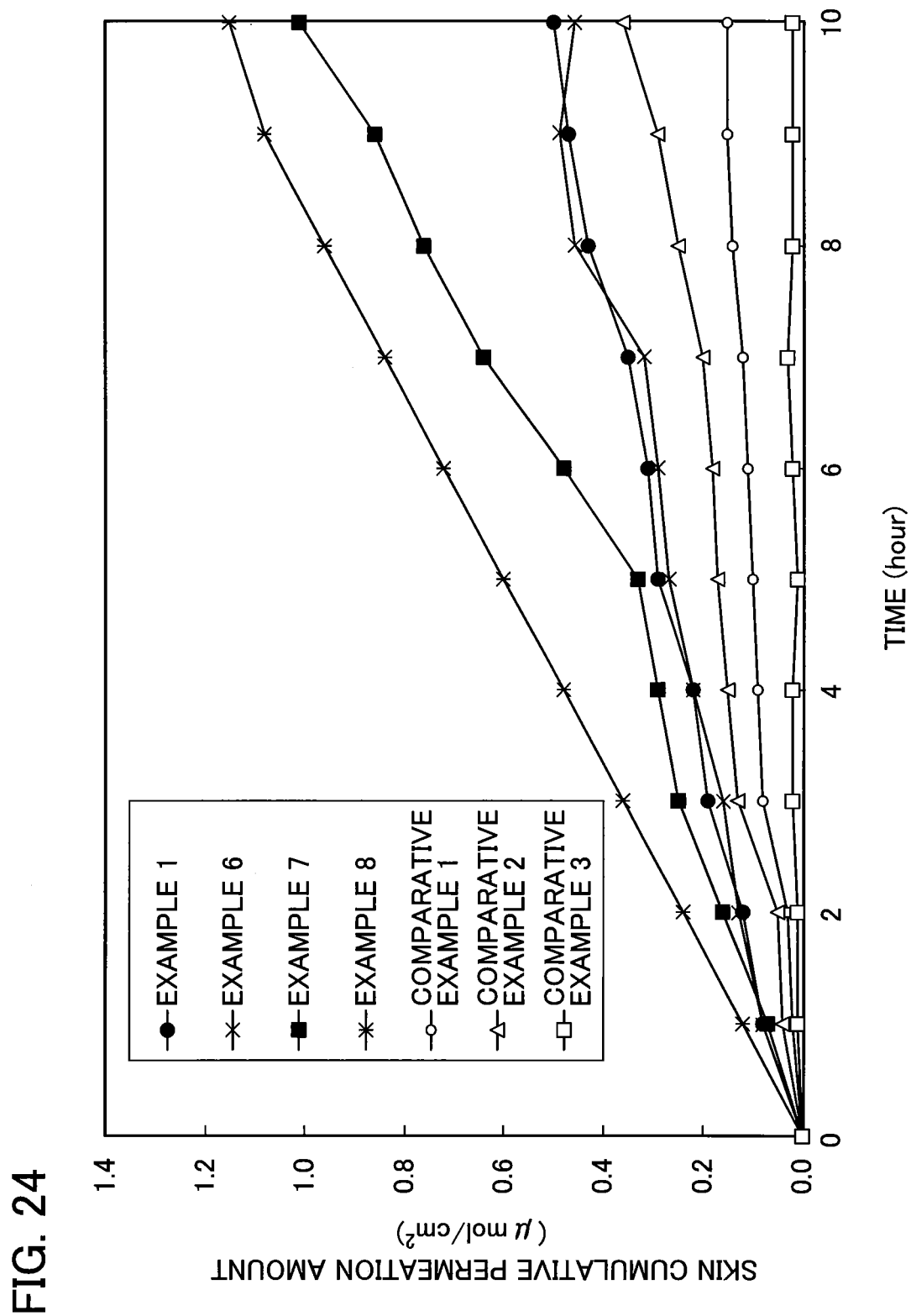
FIG. 24 is a graph illustrating measurement results.

FIG. 24 illustrates the measurement results of Example 7 and Example 8 to be described later. FIG. 24 also illustrates the measurement results of Examples 1 and 6 and Comparative Examples 1 to 3 described above.

It can be found from the measurement results illustrated in FIG. 24 that the cumulative permeation amount of L-ascorbic acid at each time in Example 7 is greater than those in Example 1 and Comparative Example 1. In Example 1, electrons moved not only via the biological tissue but also via the electrically-conductive layer 204 and this reduced the effect of the ion introduction. In Example 7, the electrically-conductive layer was divided into the positive electrode electrically-conductive layer 204A and the negative electrode electrically-conductive layer 204B. This promoted the movement of electrons via the biological tissue and the effect of the ion introduction increased.

Example 8

A configuration of the battery part 2 in Example 8 was the same as that in Example 7. Example 8 was different from Example 7 in the point that the bacterial xerogel was used for the separator 203 and the positive electrode 201 and the negative electrode 202 were fabricated by application to the positive electrode electrically-conductive layer 204A and the negative electrode electrically-conductive layer 204B.

The bacterial xerogel was synthesized by the same synthesizing method as in Example 1. The bacterial xerogel was cut into a rectangular shape with a size of 30 mm×50 mm by using a blanking blade, a laser cutter, and the like and the cut-out bacterial xerogel was used as the separator 203.

In Example 8, the positive electrode 201 and the negative electrode 202 were fabricated by using the manufacturing method of FIGS. 8 and 9. Specifically, in Example 8, the electrodes 201 and 202 were fabricated by using the slurry for the positive electrode and the slurry for the negative electrode as in Example 5. In the applying step, the slurry for the positive electrode was applied onto the positive electrode electrically-conductive layer 204A, in an area of 30 mm×20 mm to a thickness of 3 mm by using a squeegee and the slurry for the negative electrode was applied onto the negative electrode electrically-conductive layer 204B, in an area of 30 mm×20 mm to a thickness of 3 mm by using a squeegee. After the applying step, the positive electrode electrically-conductive layer 204A and the negative electrode electrically-conductive layer 204B were dried at 60° C. for 24 hours by using a thermostat chamber and the positive electrode 201 and the negative electrode 202 were obtained.

The manufacturing method, the test apparatus, and the evaluation method of the biological tissue transdermal patch 1 were the same as those in Example 1.

It can be found from the measurement results illustrated in FIG. 24 that the cumulative permeation amount of L-ascorbic acid at each time in Example 8 is greater than that in Example 7. In Example 8, since the positive electrode 201 and the negative electrode 202 were fabricated by application to the positive electrode electrically-conductive layer 204A and the negative electrode electrically-conductive layer 204B, the adhesion force of the electrodes 201 and 202 to the positive electrode electrically-conductive layer 204A and the negative electrode electrically-conductive layer 204B was great. This reduced the resistance value and the ion introduction due to the battery reaction was promoted.

As described above, in the embodiment, the biological tissue transdermal patch 1 houses the battery part 2 and the active ingredient 3 such that they do not come into contact with each other. For the use of the biological tissue transdermal patch 1, the battery part 2 and the active ingredient 3 are brought into contact with each other to start the battery reaction of the battery part 2 and the battery part 2 is attached to the biological tissue. This can suppress self-discharge of the battery part 2 in storage and enables the active ingredient 3 to be maintained in a fresh state. Thus, an excellent ion introduction can be obtained.

According to the embodiment, the carbonized bacterial cellulose or the cellulose nanofiber carbon is used for the positive electrode 201 of the battery part 2. This reduces environmental load enables easy disposal in daily life.

Although the battery part 2 and the active ingredient 3 are housed together in the plastic pack 4 while being isolated from each other in the embodiment, the battery part 2 and the active ingredient 3 may be housed and stored separately.

Note that the present invention is not limited to the embodiment described above and it is apparent that one having ordinary skill in the art can make many modifications and combinations within the technical scope of the present invention.

EXPLANATION OF THE REFERENCE NUMERALS 1 biological tissue transdermal patch
2 battery part
201 positive electrode
202 negative electrode
203 separator
203A positive electrode separator
203B negative electrode separator
204 electrically-conductive layer
204A positive electrode electrically-conductive layer
204B negative electrode electrically-conductive layer
205A upper surface water repelling layer
205B contact surface water repelling layer
205C contact portion
3 active ingredient
4 plastic pack
41 partition wall
42 battery part storage
43 active ingredient storage
100 biological tissue

The invention claimed is:

1. A biological tissue transdermal patch which is to be used by being attached to a biological tissue, comprising:
a battery part; and
an active ingredient,
wherein the battery part includes:
a positive electrode;
a negative electrode;
an electrically-conductive layer; and
a separator, wherein a first portion of the separator is arranged in contact with the positive electrode and a second portion of the separator is arranged in contact with the negative electrode,
wherein in a first configuration for storage of the biological tissue transdermal patch, the separator includes no electrolyte and the active ingredient is housed out of contact with the battery part, and wherein in a second configuration for use of the biological tissue transdermal patch, the active ingredient is brought into contact with the separator to start a battery reaction.

2. The biological tissue transdermal patch according to claim 1, further comprising a container which includes a partition wall and which houses the battery part and the active ingredient together in the container while isolating the battery part and the active ingredient from each other in the first configuration, wherein
in the second configuration for the use of the biological tissue transdermal patch, the partition wall is at least partially removed to bring the active ingredient into contact with the battery part.

3. The biological tissue transdermal patch according to claim 1, wherein
the first portion of the separator is a positive electrode separator which is arranged in contact with the positive electrode and out of contact with the negative electrode and the second portion of the separator is a negative electrode separator which is arranged in contact with the negative electrode and out of contact with the positive electrode, and
after the battery reaction is started, the biological tissue transdermal patch is configured to be used with the positive electrode separator and the negative electrode separator brought into contact with the biological tissue.

4. The biological tissue transdermal patch according to claim 3, wherein the electrically-conductive layer has a liquid repelling property.

5. The biological tissue transdermal patch according to claim 1, wherein
the electrically-conductive layer includes a positive electrode electrically-conductive layer which is arranged in contact with the positive electrode and out of contact with the negative electrode and a negative electrode electrically-conductive layer which is arranged in contact with the negative electrode and out of contact with the positive electrode, and
after the battery reaction is started, the biological tissue transdermal patch is configured to be used with the positive electrode electrically-conductive layer and the negative electrode electrically-conductive layer brought into contact with the biological tissue.

6. The biological tissue transdermal patch according to claim 1, wherein the separator is formed of xerogel.

7. The biological tissue transdermal patch according to claim 1, wherein the negative electrode contains at least one of magnesium, zinc, aluminum, iron, calcium, lithium, and sodium.

8. The biological tissue transdermal patch according to claim 1, wherein the battery reaction generates magnesium hydroxide.

9. A biological tissue transdermal patch which is to be used by being attached to a biological tissue, comprising:
a battery par; and
an active ingredient,
wherein the battery part includes:
a positive electrode;
a negative electrode;
an electrically-conductive layer; and
a separator,
wherein in a first configuration for storage of the biological tissue transdermal patch, the separator includes no electrolyte and the active ingredient is housed out of contact with the battery part,
wherein in a second configuration for use of the biological tissue transdermal patch, the active ingredient is brought into contact with the separator to start a battery reaction, and
wherein the positive electrode contains carbonized cellulose with a three-dimensional network structure.

* * * * *